US006977082B2

United States Patent
Seitz, Jr. et al.

(10) Patent No.: US 6,977,082 B2
(45) Date of Patent: Dec. 20, 2005

(54) HIGH EFFICACY ANTIBACTERIAL COMPOSITIONS HAVING ENHANCED ESTHETIC AND SKIN CARE PROPERTIES

(75) Inventors: Earl P. Seitz, Jr., Scottsdale, AZ (US); Gregory A. Konishi, Scottsdale, AZ (US); Andrea Lynn Waggoner, Mesa, AZ (US); Timothy J. Taylor, Phoenix, AZ (US); Janice Lynn Fuls, Fountain Hills, AZ (US); Sydney Lindsay Schilcher, Glendale, AZ (US); DeAnn Marie Pospisil Davis, Fountain Hills, AZ (US)

(73) Assignee: The Dial Corporation, Scottsdale, AZ (US)

( * ) Notice: Subject to any disclaimer, the term of this patent is extended or adjusted under 35 U.S.C. 154(b) by 233 days.

(21) Appl. No.: 10/103,246

(22) Filed: Mar. 21, 2002

(65) Prior Publication Data

US 2003/0069317 A1 Apr. 10, 2003

Related U.S. Application Data

(60) Provisional application No. 60/279,949, filed on Mar. 29, 2001.

(51) Int. Cl.⁷ .............................. A01N 25/00; A61K 7/00
(52) U.S. Cl. ....................................... 424/405; 424/401
(58) Field of Search ................................... 424/401, 405

(56) References Cited

U.S. PATENT DOCUMENTS

| 5,929,024 | A | * | 7/1999 | Stringer et al. ............. 510/504 |
| 5,968,539 | A | * | 10/1999 | Beerse et al. ................ 424/405 |
| 6,107,261 | A | * | 8/2000 | Taylor et al. ................ 510/131 |
| 6,204,230 | B1 | * | 3/2001 | Taylor et al. ................ 510/131 |
| 6,451,748 | B1 | * | 9/2002 | Taylor et al. ................ 510/131 |
| 6,616,922 | B2 | * | 9/2003 | Taylor et al. ............. 424/70.28 |

OTHER PUBLICATIONS

CTFA I"International Cosmetic Ingredient dictionary and Handbook, 1997, pp. 235–236.*

* cited by examiner

*Primary Examiner*—Shengjun Wang
(74) *Attorney, Agent, or Firm*—Marshall, Gerstein & Borun LLP

(57) ABSTRACT

Antibacterial compositions having high antibacterial effectiveness and excellent esthetic properties are disclosed. The compositions also impart skin conditioning properties and improved feel to cleansed skin. The antibacterial compositions contain a phenolic antibacterial agent, a surfactant, esthetic enhancers, skin care ingredients, and water, wherein a percent saturation of the antibacterial agent in the aqueous phase of the composition is at least 25%.

22 Claims, 3 Drawing Sheets

Panel Terminations per Wash Session for the Volar Forearm Only

Total Panel All Sites Drop per Session

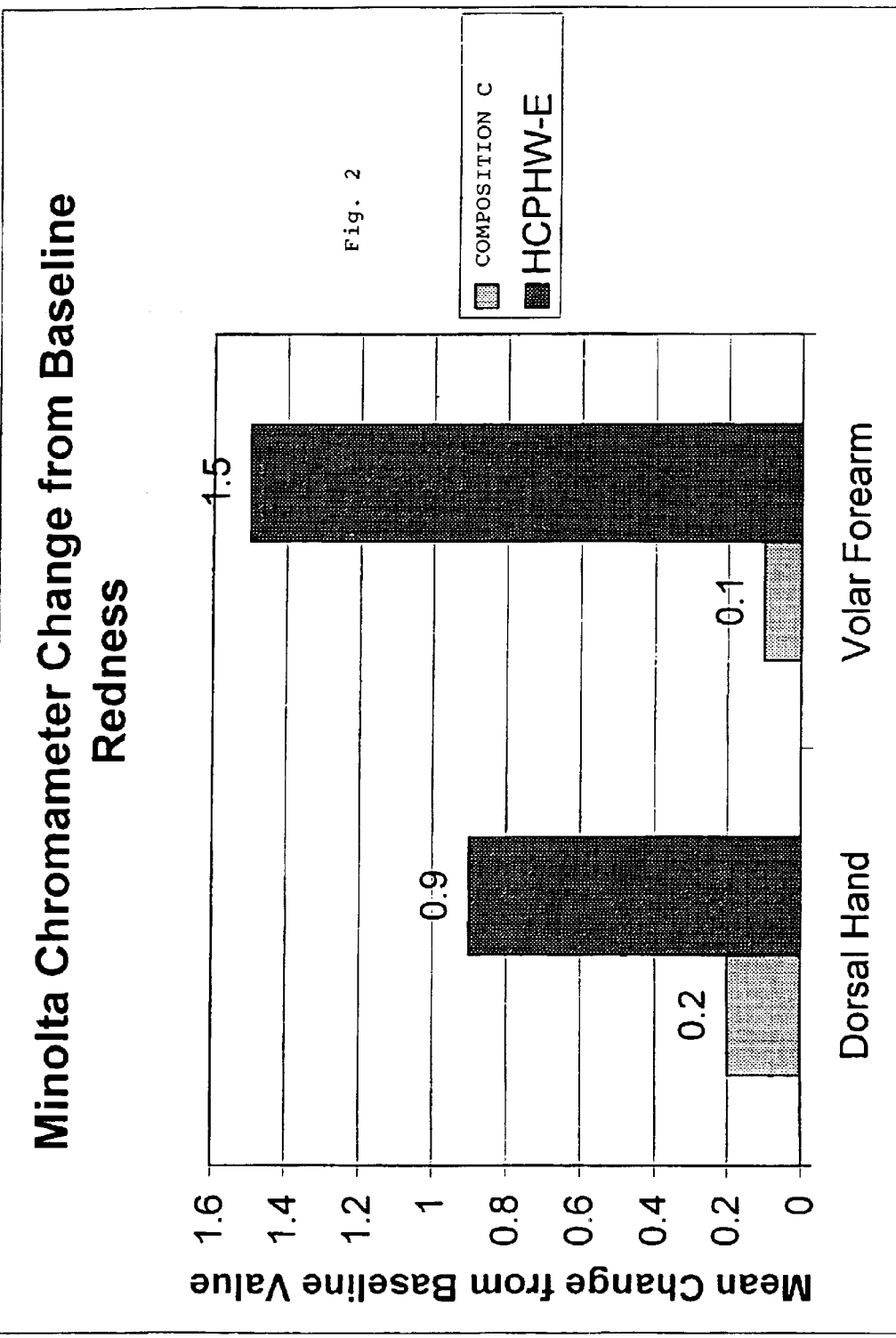

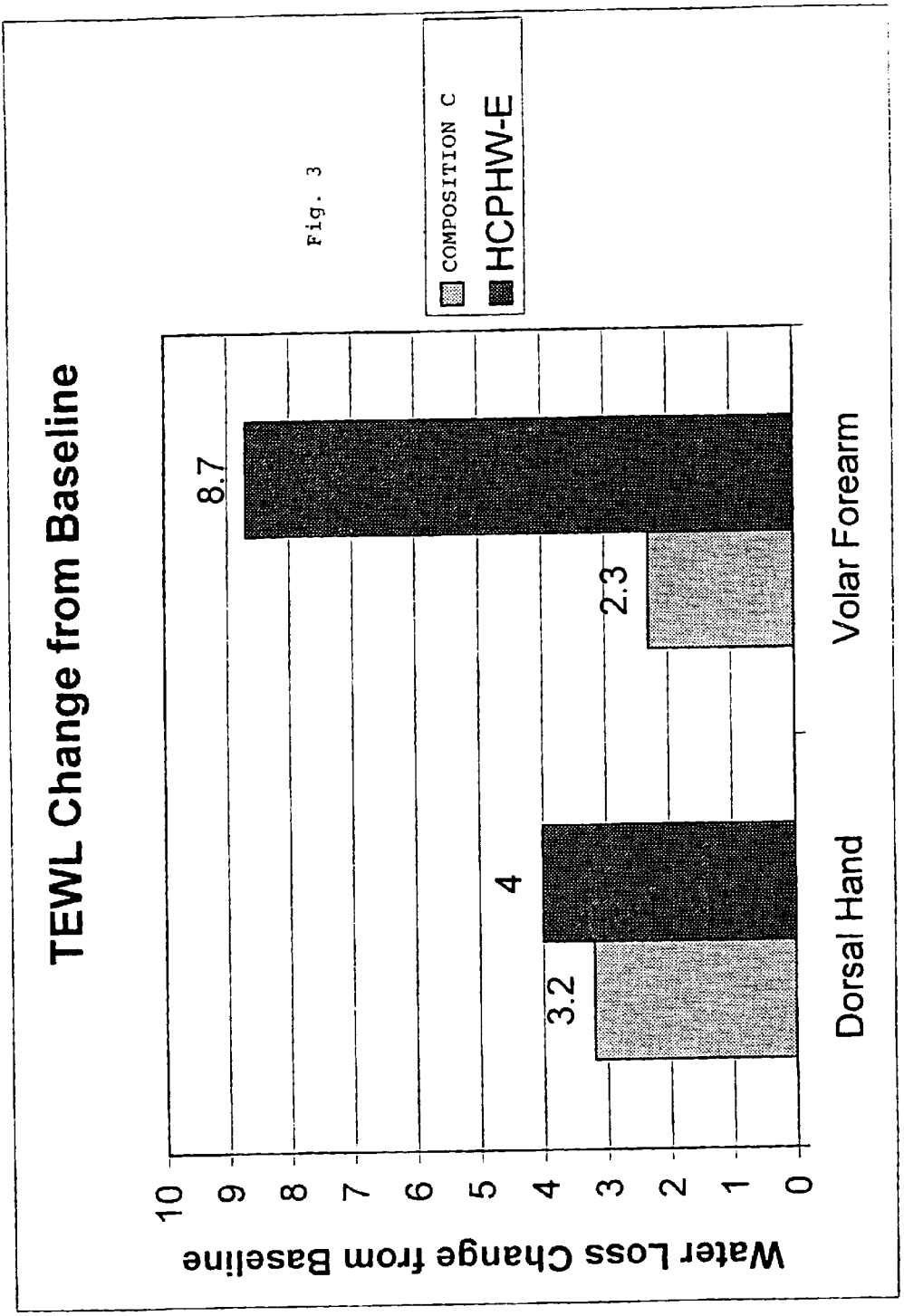

HIGH EFFICACY ANTIBACTERIAL COMPOSITIONS HAVING ENHANCED ESTHETIC AND SKIN CARE PROPERTIES

CROSS REFERENCE TO RELATED APPLICATION

This application claims the benefit of U.S. provisional patent application Ser. No. 60/279,949, filed Mar. 29, 2001.

FIELD OF THE INVENTION

The present invention relates to antibacterial compositions, like personal care compositions, having high antibacterial effectiveness and excellent esthetic properties, such as foam generation, foam stability, and a capability of imparting skin care properties to cleansed skin. More particularly, the present invention relates to antibacterial compositions comprising an antibacterial agent, a surfactant, a hydrotrope, a hydric solvent, esthetics-enhancing ingredients, and optional skin care ingredients, and that provide a substantial reduction, e.g., greater than 99%, in Gram positive and Gram negative bacteria populations within one minute.

BACKGROUND OF THE INVENTION

Antibacterial personal care compositions are known in the art. Especially useful are antibacterial cleansing compositions, which typically are used to cleanse the skin and to destroy bacteria and other microorganisms present on the skin, especially the hands, arms, and face of the user.

Antibacterial compositions are used, for example, in the health care industry, food service industry, meat processing industry, and in the private sector by individual consumers. The wide-spread use of antibacterial compositions indicates the importance consumers place on controlling bacteria and other microorganism populations on skin. It is important, however, that antibacterial compositions provide a substantial and broad spectrum reduction in microorganism populations quickly and without problems associated with toxicity and skin irritation.

In particular, antibacterial cleansing compositions typically contain an active antibacterial agent, a surfactant, and various other ingredients, for example, dyes, fragrances, pH adjusters, thickeners, and the like, in an aqueous carrier. Several different classes of antibacterial agents have been used in antibacterial cleansing compositions. Examples of antibacterial agents include a bisguanidine (e.g., chlorhexidine digluconate), diphenyl compounds, benzyl alcohols, trihalocarbanilides, quaternary ammonium compounds, ethoxylated phenols, and phenolic compounds, such as halo-substituted phenolic compounds, like PCMX (i.e., p-chloro-m-xylenol) and triclosan (i.e., 2,4,4'-tri-chloro-2'hydroxy-diphenylether). Present-day antimicrobial compositions based on such antibacterial agents exhibit a wide range of antibacterial activity, ranging from low to high, depending on the microorganism to be controlled and the particular antibacterial composition.

Most commercial antibacterial compositions, however, generally offer a low to moderate antibacterial activity. Antibacterial activity is assessed against a broad spectrum of microorganisms, including both Gram positive and Gram negative microorganisms. The log reduction, or alternatively the percent reduction, in bacterial populations provided by the antibacterial composition correlates to antibacterial activity. A log reduction of 3–5 is most preferred, a 1–3 reduction is preferred, whereas a log reduction of less than 1 is least preferred, for a particular contact time, generally ranging from 15 seconds to 5 minutes. Thus, a highly preferred antibacterial composition exhibits a 3–5 log reduction against a broad spectrum of micro-organisms in a short contact time. Prior disclosures illustrate attempts to provide such antibacterial compositions, which, to date, do not provide the rapid, broad range control of microorganisms desired by consumers.

It should be noted that high log reductions have been achieved at pH values of 4 and 9, but such log reductions are attributed at least in part to these relatively extreme pH values. Compositions having such pH values can irritate the skin and other surfaces, and, therefore, typically are avoided. It has been difficult to impossible to achieve a high log reduction using an antibacterial composition having a neutral pH of about 5 to about 8, and especially about 6 to about 8.

However, highly efficacious antibacterial compositions suffer in comparison to regular (i.e., nonantibacterial) personal care compositions with respect to acceptable consumer properties, especially foam characteristics and imparting skin care properties, such as skin conditioning. It also is difficult to provide phase stable, highly efficacious antibacterial compositions having consumer-acceptable esthetics. Further, present-day antibacterial personal care compositions do not provide an effective antibacterial activity, especially against pathogenic Gram negative bacteria. Thus, a need exists for phase stable, efficacious antibacterial personal care compositions containing skin care ingredients, and that further are consumer acceptable.

An example of patents and published applications disclosing compositions comprising triclosan, surfactants, solvents, chelating agents, thickeners, buffering agents, and water is WO 98/01110. WO 98/01110 is directed to reducing skin irritation by employing a reduced amount of surfactant.

Fendler et al. U.S. Pat. No. 5,635,462 discloses compositions comprising PCMX and selected surfactants. The compositions disclosed therein are devoid of anionic surfactants and nonionic surfactants.

WO 97/46218 and WO 96/06152 disclose compositions based on triclosan, organic acids or salts, hydrotropes, and hydric solvents.

EP 0 505 935 discloses compositions containing PCMX in combination with nonionic and anionic surfactants, particularly nonionic block copolymer surfactants.

WO 95/32705 discloses a mild surfactant combination that can be combined with antibacterial compounds, like triclosan.

WO 95/09605 discloses antibacterial compositions containing anionic surfactants and alkyl-polyglycoside surfactants.

WO 98/55096 discloses antimicrobial wipes having a porous sheet impregnated with an antibacterial composition containing an active antimicrobial agent, an anionic surfactant, an acid, and water, wherein the composition has a pH of about 3.0 to about 6.0.

Glenn, Jr. et al. U.S. Pat. No. 5,885,948 discloses a stress stable, lathering skin cleansing composition containing about one to 30 parts lipid skin moisturizing agents.

Beerse et al. U.S. Pat. Nos. 5,968,539; 6,106,851; and 6,113,933 disclose antibacterial compositions having a pH of about 3 to about 6. The compositions contain an antibacterial agent, an anionic surfactant, and a proton donor.

N. A. Allawala et al., *J. Amer. Pharm. Assoc.—Sci. Ed.*, Vol. XLII, no. 5, pp. 267–275, (1953) discusses the antibacterial activity of active antibacterial agents in combination with surfactants.

A. G. Mitchell, *J. Pharm. Pharmacol.*, Vol. 16, pp. 533–537, (1964) discloses compositions containing PCMX and a nonionic surfactant that exhibit antibacterial activity. The compositions disclosed in the Mitchell publication exhibit antibacterial activity in at least 47 minutes contact time, thus the compositions are not highly effective.

Prior disclosures have not addressed the issue of providing an antibacterial composition that (a) affords an effective, fast, and broad spectrum control of bacteria at a neutral pH of about 5 to about 8, and especially at about 6 to about 8, (b) is phase stable, (c) exhibits excellent esthetic properties, such as a stable, copious foam generation, and (d) imparts skin care properties to cleansed skin. In addition to the above, prior disclosures also have not addressed providing a composition of sufficiently low viscosity for use with a self-foaming pump.

An efficacious antibacterial composition has been difficult to achieve because of the properties of the antibacterial agents and the effects of a surfactant, a hydrotrope, and a hydric solvent on an antibacterial agent. One such efficacious antibacterial composition is discussed in Taylor et al. U.S. Pat. No. 6,107,261, incorporated herein by reference. This patent discloses a highly efficacious antibacterial composition against Gram negative and Gram positive bacteria, and containing a high percent (at least 25%) saturation of a phenolic antibacterial agent. The positive effects of a higher percent of saturation of antibacterial agent is fully discussed in U.S. Pat. No. 6,107,261.

A need now exists for an antibacterial composition that is highly efficacious against a broad spectrum of Gram positive and Gram negative bacteria in a short time period, wherein the antibacterial activity is attributed primarily, or solely, to the presence of the active antibacterial agent in the composition, and has consumer-acceptable esthetic properties with respect to phase stability, feel, foam generation and stability, and imparting skin care properties. The present invention is directed to such efficacious and esthetically pleasing antibacterial compositions.

The development of such compositions is difficult because of factors such as a) the need for a high antimicrobial efficacy even in the presence of esthetic enhancing and skin care additives, b) the need to maintain a relatively high % saturation of the antibacterial agent, and c) the difficulty in formulating a high-foaming composition in the presence of significant amounts of a hydrotrope and hydric solvent. Unlike present-day commercial compositions and compositions disclosed in the prior art, the variety, type, and amounts of esthetic enhancing and skin care additives that can be incorporated in the present compositions are varied and unexpected, and a high percent saturation of antibacterial agent can be maintained.

In addition, antibacterial composition viscosity also is critical for particular applications. For example, a preferred method of using the composition is with a self-foaming pump. If the viscosity of the composition is too high (e.g., greater than about 50 centipoise), the composition cannot be pumped through a preferred foaming device. Finally, foam generation and stability also are important for consumer acceptability. Compositions of the present invention exhibit excellent viscosity, enhanced foam volume, creaminess, and slip during human use tests. This is especially important for application of the antibacterial composition to dry hands through a foaming pump, followed by about 30 seconds lathering, and completed by rinsing with water. This type of application provides the highest antibacterial effect.

SUMMARY OF THE INVENTION

The present invention is directed to antibacterial compositions that provide a substantial reduction in Gram positive and Gram negative bacteria in less than about one minute. More particularly, the present invention is directed to antimicrobial compositions containing an active antibacterial agent, a surfactant, and water, in addition to ingredients such as emollients, humectants, and foam stabilizers to impart esthetics to the composition and skin care properties to cleansed skin. The antibacterial agent is present in the composition in an amount of at least 25% of saturation, when measured at room temperature. The present antimicrobial compositions are phase stable, and can be designed to have a viscosity suitable for a variety of end uses, including a composition for use with a self-foaming pump and a composition that is applied to the skin neat, lathered to cleanse the skin and kill bacteria, followed by rinsing from the skin.

Accordingly, one aspect of the present invention is to provide an antibacterial composition, wherein the composition comprises:

(a) about 0.001% to about 10%, by weight, of an antimicrobial agent;

(b) about 0.1% to about 40%, by weight, of a surfactant selected from the group consisting of an anionic surfactant, a cationic surfactant, a nonionic surfactant, an ampholytic surfactant, and mixtures thereof;

(c) about 1% to about 40%, by weight, of a hydrotrope;

(d) about 1% to about 25%, by weight, of a water-soluble hydric solvent; and (e) 0% to about 5%, by weight, of a skin care agent;

(f) 0% to about 5%, by weight, of a foam stabilizer;

(g) 0% to about 5%, by weight, of a humectant; and (h) water, wherein the composition contains at least one of (e), (f), and (g), and wherein the antimicrobial agent is present in the composition in an amount of at least 25% of saturation concentration, when measured at room temperature.

Another aspect of the present invention is to provide an antibacterial composition that exhibits a log reduction against Gram positive bacteria (i.e., *S. aureus*) of at least 2 after 30 seconds of contact.

Still another aspect of the present invention is to provide an antibacterial composition that exhibits a log reduction against Gram negative bacteria (i.e., *E. coli*) of at least 2.5 after 30 seconds of contact.

Another aspect of the present invention is to provide an antibacterial composition that exhibits a substantial log reduction against Gram positive and Gram negative bacteria, and has a pH of about 5 to about 8.

A present antibacterial composition is phase stable, and typically has a viscosity of about 0.1 to about 50 centipoise (cp). However, in the presence of an optional thickener, the viscosity can be up to about 10,000. The present compositions also exhibit excellent esthetic properties, such as foam height and foam stability. The present compositions further impart skin conditioning and improved skin feel to cleansed skin. These improved esthetic and skin care properties are unexpected in antibacterial compositions because skin care and esthetic ingredients are difficult to incorporate into antibacterial compositions, and especially difficult to incorporate without adversely affecting the antibacterial efficacy of the composition.

Another aspect of the present invention is to provide consumer products based on an antibacterial composition of the present invention, for example, a skin cleanser, a body splash, a surgical scrub, a wound care agent, a hand sanitizer gel, a disinfectant, a mouth wash, a pet shampoo, a hard surface sanitizer, and the like. The present compositions can be applied, then either rinsed off, wiped off, or allowed to remain on the skin.

A further aspect of the present invention is to provide a method of reducing the Gram positive and/or Gram negative bacteria populations on animal tissue, including human tissue, by contacting the tissue, like the dermis, with a composition of the present invention for a sufficient time, such as about 15 seconds to 5 minutes, to reduce the bacteria level to a desired level.

The above and other novel aspects and advantages of the present invention are illustrated in the following, nonlimiting detailed description of the preferred embodiments.

BRIEF DESCRIPTION OF THE DRAWINGS

FIG. 2 contains bar graphs showing the change in baseline for a skin redness study using Composition C and HCPHW-E; and FIG. 3 contains bar graphs showing the water loss change for a study using Composition C and HCPHW-E.

DETAILED DESCRIPTION OF THE PREFERRED EMBODIMENTS

Figure 1A:
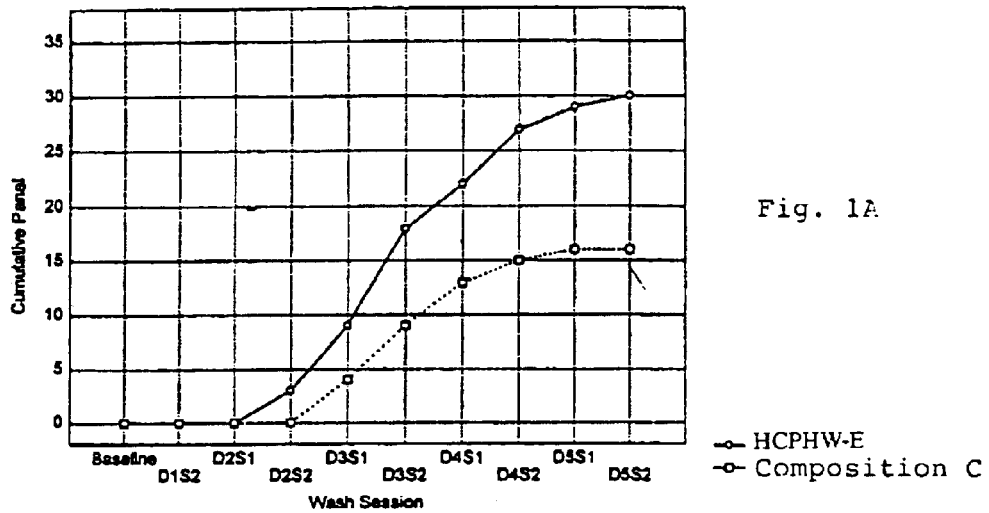
FIGS. 1A and 1B are graphs of number of panelists vs. wash session showing the number of panelists that terminated the study.

Personal care products incorporating an active antibacterial agent have been known for many years. Since the introduction of antibacterial personal care products, many claims have been made that such products provide antibacterial properties. However, to be most effective, an antibacterial composition should provide a high log reduction against a broad spectrum of organisms in as short a contact time as possible.

The antibacterial composition also should exhibit excellent esthetic properties and impart skin care properties in order to achieve consumer acceptance. The features of antibacterial efficacy, esthetics, and skin care often are competing, wherein enhancing one feature is detrimental to the other. The present invention is directed to antibacterial compositions that unexpectedly exhibit all of these features.

As presently formulated, most commercial liquid antibacterial soap compositions provide a poor to marginal time kill efficacy, i.e., rate of killing bacteria. Table 1 summarizes the kill efficacy of commercial products, each of which contains about 0.2% to 0.3%, by weight, triclosan (an antibacterial agent).

TABLE 1

Time Kill Efficacy of Commercial Liquid Hand Soaps
(log reduction after 1 minute contact time)

| Product | Gram positive S. aureus | Gram negative E. Coli | Gram negative K. pneum. |
|---|---|---|---|
| Commercial Product A | 1.39 | 0.00 | 0.04 |
| Commercial Product B | 2.20 | 0.00 | 0.01 |
| Commercial Product C | 1.85 | 0.00 | 0.00 |
| Commercial Product D | 2.79 | 0.26 | — |

Present-day products especially lack efficacy against Gram negative bacteria, such as E. coli, which are of particular concern to human health. For example, note that Commercial Product D of Table 1, referred to as a "moisturizing antimicrobial" product is ineffective versus E. coli in a time-kill test. The present invention, therefore, is directed to antibacterial compositions having an exceptionally high broad spectrum antibacterial efficacy, as measured by a rapid kill of bacteria (i.e., time kill), which is to be distinguished from persistent kill, and that provides consumer-acceptable esthetic properties.

The present antibacterial compositions provide significantly improved time kill efficacy compared to prior compositions. The basis of this improved time kill is the discovery that the antimicrobial efficacy of an active agent can be correlated to the rate at which the agent has access to an active site on the microbe. The driving force that determines the rate of agent transport to the site of action is the difference in chemical potential between the site at which the agent acts and the external aqueous phase. Alternatively stated, the microbicidal activity of an active agent is proportional to its thermodynamic activity in the external phase. Accordingly, thermodynamic activity, as opposed to concentration, is the more important variable with respect to antimicrobial efficacy. Thermodynamic activity is conveniently correlated to the percent saturation of the active antibacterial agent in the continuous aqueous phase of the composition. This feature is discussed fully in U.S. Pat. No. 6,107,621, incorporated herein by reference.

The present compositions are antibacterial compositions having an improved effectiveness against both Gram negative and Gram positive bacteria, that exhibit a rapid bacteria kill, that exhibit excellent esthetics, and that impart skin conditioning and improved feel to cleansed skin. As illustrated in the following embodiments, an antibacterial composition of the present invention comprises: (a) about 0.001% to about 10%, by weight, of an antibacterial agent; (b) about 0.1% to about 40%, by weight, of a surfactant; (c) about 1% to about 40%, by weight, of a hydrotrope; (d) about 1% to about 25%, by weight, of a hydric solvent; (e) 0% to about 5%, by weight, of a skin care agent; (f) 0% to about 2%, by weight, of a foam stabilizer; (g) 0% to about 5%, by weight, of a humectant; and (h) water, wherein the composition contains at least one of (e), (f), and (g).

The compositions have a percent saturation of antibacterial agent in the continuous aqueous phase of at least about 25%, when measured at room temperature. The compositions exhibit a log reduction against Gram positive bacteria of at least about 2 after 30 seconds contact. The compositions exhibit a log reduction against Gram negative bacteria of at least about 2.5 after 30 seconds contact. The compositions also exhibit excellent composition esthetics, e.g., foam characteristics, and viscosity. The compositions further impart skin conditioning properties and improved feel to cleansed skin.

Embodiments of the present invention comprise (a) an active antibacterial agent, (b) a surfactant, (c) a hydrotrope, (d) a hydric solvent, (e) at least one of a skin care agent, a foam stabilizer, and a humectant, and (f) water. The presence of a hydric solvent, hydrotrope, skin care agent, foam stabilizer, and humectant do not adversely affect the antimicrobial properties of the composition. The compositions are phase stable, and exhibit excellent esthetic properties, such as foam generation and stability, and impart excellent skin conditioning properties and skin feel. The compositions can further include additional optional ingredients disclosed hereafter, such as thickeners, preservatives, pH adjusters, dyes, and perfumes.

In particular, the present invention is directed to antibacterial compositions, especially for use in personal care, but also suitable as disinfectants, surgical scrubs, hospital hand wash products, hand sanitizer gels, wound care agents, and the like. The present compositions comprise about 0.001% to about 10% of a phenolic antibacterial agent, preferably triclosan or PCMX, dissolved in an aqueous vehicle and further containing a surfactant, solvent, hydrotrope, and at least one of a skin care agent, foam stabilizer, and humectant. The surfactant, solvents, and hydrotropes are present in amounts such that the percent saturation of the phenolic antibacterial agent in the composition is at least 25%, preferably greater than about 50%, and most preferably greater than about 95% (see U.S. Pat. No. 6,107,261). The foam stabilizing, skin care, and humectant additives are selected from compounds including, but not limited to, polymers, protein derivatives, silicone derivatives, ethoxylated derivatives, long-chain fatty materials, and lipid-like materials. The present compositions exhibit new and unexpected properties, like mildness, skin after-feel, foaming properties, and other properties required, or at least desired, by consumers.

As demonstrated in more detail hereafter, a preferred embodiment contains, by weight, about 0.3% to about 1.0% triclosan, about 5% to about 15% dipropylene glycol, about 10% to about 40% sodium xylene sulfonate, about 0.5% to about 5% ammonium lauryl sulfate, 0% to about 5% cocamidopropyl betaine, and one or more of 0% to about 3% sodium PCA, 0% to about 0.5% cetyl or cetearyl alcohol, 0% to about 0.5% polyquaternium-10, 0% to about 5% glycerin, and 0% to about 1% aloe.

A. Antibacterial Agent

An antibacterial agent is present in a composition of the present invention in an amount of about 0.001% to about 10%, and preferably about 0.01% to about 5%, by weight of the composition. To achieve the full advantage of the present invention, the antibacterial agent is present in an amount of about 0.05% to about 2%, by weight, of the composition.

The antibacterial compositions can be ready to use compositions, which typically contain 0.001% to about 2%, preferably 0.01% to about 1.5%, and most preferably about 0.05% to about 1%, of an antibacterial agent, by weight of the composition. The antibacterial compositions also can be formulated as concentrates that are diluted before use with one to about 100 parts water to provide an end use composition. The concentrated compositions typically contain greater than about 0.1% and up to about 10%, by weight, of the antibacterial agent. Applications also are envisioned wherein the end use composition contains greater than 2%, by weight, of the antibacterial agent.

As discussed in U.S. Pat. No. 6,107,261, the absolute amount of antibacterial agent present in the composition is not as important as the amount of available antibacterial agent in the composition. The amount of available antibacterial agent in the composition is related to the identity and amount of In ingredients in the composition.

To achieve the desired bacteria kill in a short contact time, like 15 to 60 seconds, the composition contains an amount of antibacterial agent that is at least about 25%, and preferably at least about 50%, of the saturation concentration of the antibacterial agent in the composition, when measured at room temperature. To achieve the full advantage of the present invention, the composition is at least 75%, and more preferably about 95% to 100%, saturated with the antibacterial agent. The method of determining percent saturation of antibacterial agent in the composition is disclosed hereafter.

The antimicrobial agents useful in the present invention are phenolic compounds exemplified by the following classes of compounds:

(a) 2-Hydroxydiphenyl Compounds

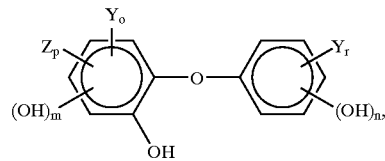

wherein Y is chlorine or bromine, Z is $SO_2H$, $NO_2$, or $C_1$–$C_4$ alkyl, r is 0 to 3, o is 0 to 3, p is 0 or 1, m is 0 or 1, and n is 0 or 1.

In preferred embodiments, Y is chlorine or bromine, m is 0, n is 0 or 1, o is 1 or 2, r is 1 or 2, and p is 0.

In especially preferred embodiments, Y is chlorine, m is 0, n is 0, o is 1, r is 2, and p is 0.

A particularly useful 2-hydroxydiphenyl compound has the structure:

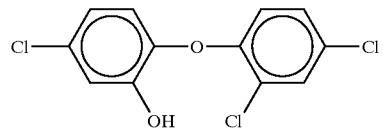

having the adopted name, triclosan, and available commercially under the tradename IRGASAN DP300, from Ciba Specialty Chemicals Corp., Greensboro, N.C. Another useful 2-hydroxydiphenyl compound is 2,2'-dihydroxy-5,5'-dibromo-diphenyl ether. Additional bisphenolic compounds are disclosed in U.S. Pat. No. 6,113,933, incorporated herein by reference.

(b) Phenol Derivatives

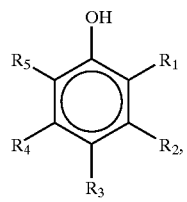

wherein $R_1$ is hydro, hydroxy, $C_1$–$C_4$ alkyl, chloro, nitro, phenyl, or benzyl; $R_2$ is hydro, hydroxy, $C_1$–$C_6$ alkyl, or halo; $R_3$ is hydro, $C_1$–$C_6$ alkyl, hydroxy, chloro, nitro, or a sulfur in the form of an alkali metal salt or ammonium salt; $R_4$ is hydro or methyl, and $R_5$ is hydro or nitro. Halo is bromo or, preferably, chloro.

Specific examples of phenol derivatives include, but are not limited to, chlorophenols (o-, m-, p-), 2,4-dichlorophenol, p-nitrophenol, picric acid, xylenol, p-chloro-m-xylenol, cresols (o-, m-, p-), p-chloro-m-cresol, pyrocatechol, resorcinol, 4-n-hexylresorcinol, pyrogallol, phloroglucin, carvacrol, thymol, p-chlorothymol, o-phenylphenol, o-benzylphenol, p-chloro-o-benzylphenol, phenol, 4-ethylphenol, and 4-phenolsulfonic acid. Other phenol derivatives are listed in WO 98/55096 and U.S. Pat. No. 6,113,933, incorporated herein by reference.

(c) Diphenyl Compounds

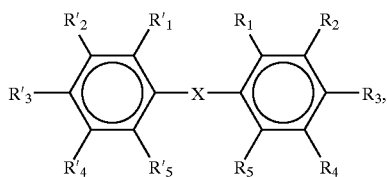

wherein X is sulfur or a methylene group, $R_1$ and $R'_1$ are hydroxy, and $R_2$, $R'_2$, $R_3$, $R'_3$, $R_4$, $R'_4$, $R_5$, and $R'_5$, independent of one another, are hydro or halo. Specific, nonlimiting examples of diphenyl compounds are hexachlorophene, tetrachlorophene, dichlorophene, 2,3-dihydroxy-5,5'-dichlorodiphenyl sulfide, 2,2'-dihydroxy-3,3',5,5'-tetrachlorodiphenyl sulfide, 2,2'-dihydroxy-3,5',5,5', 6,6'-hexachlorodiphenyl sulfide, and 3,3'-dibromo-5,5'-dichloro-2,2'-dihydroxydiphenylamine. Other diphenyl compounds are listed in WO 98/55096, incorporated herein by reference.

B. Surfactant

In addition to the antibacterial agent, a present antimicrobial composition also contains a surfactant. The surfactant is present in an amount of about 0.1% to about 40%, and preferably about 0.3% to about 20%, by weight, of the composition. To achieve the full advantage of the present invention, the antibacterial composition contains about 0.5% to about 15%, by weight, of the surfactant.

Ready-to-use compositions typically contain about 0.1% to about 10%, preferably about 0.3% to about 5%, and most preferably, 0.5% to about 3%, by weight, of the composition. Concentrated compositions suitable for dilution typically contain greater than about 5%, by weight, of a surfactant.

The amount of surfactant present in the composition is related to the amount and identity of the antibacterial agent in the composition and to the identity of the surfactant. The amount of surfactant is determined such that the percent saturation of the antibacterial agent in the composition is at least about 50%, preferably at least about 75%, and most preferably at least about 95% up to 100%.

The surfactant can be an anionic surfactant, a cationic surfactant, a nonionic surfactant, or a compatible mixture of surfactants. The surfactant also can be an ampholytic or amphoteric surfactant, which have anionic or cationic properties depending upon the pH of the composition.

The antibacterial compositions, therefore, can contain any anionic surfactant having a hydrophobic moiety, such as a carbon chain including about 8 to about 30 carbon atoms, and particularly about 12 to about 20 carbon atoms, and further has a hydrophilic moiety, such as sulfate, sulfonate, carbonate, phosphate, or carboxylate. Often, the hydrophobic carbon chain is etherified, such as with ethylene oxide or propylene oxide, to impart a particular physical property, such as increased water solubility or reduced surface tension to the anionic surfactant.

Therefore, suitable anionic surfactants include, but are not limited to, compounds in the classes known as alkyl sulfates, alkyl ether sulfates, alkyl ether sulfonates, sulfate esters of an alkylphenoxy polyoxyethylene ethanol, alpha-olefin sulfonates, beta-alkoxy alkane sulfonates, alkylaryl sulfonates, alkyl monoglyceride sulfates, alkyl monoglyceride sulfonates, alkyl carbonates, alkyl ether carboxylates, fatty acids, sulfosuccinates, sarcosinates, octoxynol or nonoxynol phosphates, taurates, fatty taurides, fatty acid amide polyoxyethylene sulfates, isethionates, or mixtures thereof.

Additional anionic surfactants are listed in McCutcheon's Emulsifiers and Detergents, 1993 Annuals, (hereafter McCutcheon's), McCutcheon Division, MC Publishing Co., Glen Rock, N.J., pp. 263–266, incorporated herein by reference. Numerous other anionic surfactants, and classes of anionic surfactants, are disclosed in Laughlin et al. U.S. Pat. No. 3,929,678, incorporated herein by reference.

Examples of anionic surfactants include a $C_8$–$C_{18}$ alkyl sulfate, a $C_8$–$C_{18}$ fatty acid salt, a $C_8$–$C_{18}$ alkyl ether sulfate having one or two moles of ethoxylation, a $C_8$–$C_{18}$ alkamine oxide, a $C_8$–$C_{18}$ alkyl sarcosinate, a $C_8$–$C_{18}$ sulfoacetate, a $C_8$–$C_{18}$ sulfosuccinate, a $C_8$–$C_{18}$ alkyl diphenyl oxide disulfonate, a $C_8$–$C_{18}$ alkyl carboxylate, a $C_8$–$C_{18}$ alpha-olefin sulfonate, a methyl ester sulfonate, and mixtures thereof. The $C_8$–$C_{18}$ alkyl group contains eight to sixteen carbon atoms, and can be straight chain (e.g., lauryl) or branched (e.g., 2-ethylhexyl). The cation of the anionic surfactant can be an alkali metal (preferably sodium or potassium), ammonium, $C_1$–$C_4$ alkylammonium (mono-, di-, tri), or $C_1$–$C_3$ alkanolammonium (mono-, di-, tri-). Lithium and alkaline earth cations (e.g., magnesium) can be used, but antibacterial efficacy is reduced.

Specific surfactants include, but are not limited to, lauryl sulfates, octyl sulfates, 2-ethylhexyl sulfates, lauramine oxide, decyl sulfates, tridecyl sulfates, cocoates, lauroyl sarcosinates, lauryl sulfosuccinates, linear $C_{10}$ diphenyl oxide disulfonates, lauryl sulfosuccinates, lauryl ether sulfates (1 and 2 moles ethylene oxide), myristyl sulfates, oleates, stearates, tallates, cocamine oxide, decylamine oxide, myristamine oxide, ricinoleates, cetyl sulfates, and similar surfactants.

The antibacterial compositions also can contain nonionic surfactants. Typically, a nonionic surfactant has a hydrophobic base, such as a long chain alkyl group or an alkylated aryl group, and a hydrophilic chain comprising a sufficient number (i.e., 1 to about 30) of ethoxy and/or propoxy moieties. Examples of classes of nonionic surfactants include ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$–$C_{18}$) acids, condensation products of ethylene oxide with long chain amines or amides, and mixtures thereof.

Exemplary nonionic surfactants include, but are not limited to, methyl gluceth-10, PEG-20 methyl glucose distearate, an alkyl polyglucoside (APG), like decyl polyglucoside or lauryl polyglucoside, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$–$C_{22}$) alcohol, including 7 to 20 ethylene oxide moieties, polyoxyethylene-20 isohexadecyl ether, polyoxyethylene-23 glycerol laurate, polyoxy-ethylene-20 glyceryl stearate, PPG-10 methyl glucose ether, PPG-20 methyl glucose ether, polyoxyethylene-20 sorbitan mono-esters, polyoxyethylene-80 castor oil, polyoxyethylene-15 tridecyl ether, polyoxy-ethylene-6 tridecyl ether, PEG 600 dioleate, PEG 400 dioleate, and mixtures thereof.

Numerous other nonionic surfactants are disclosed in McCutcheonrs Detergents and Emulsifiers, 1993 Annuals, published by McCutcheon Division, MC Publishing Co., Glen Rock, N.J., pp. 1–246 and 266–272; in the *CTFA*

*International Cosmetic Ingredient Dictionary, Fourth Ed.*, Cosmetic, Toiletry and Fragrance Association, Washington, D.C. (1991) (hereinafter the CTFA Dictionary) at pages 1–651; and in the *CTFA Handbook*, at pages 86–94, each incorporated herein by reference.

In addition to anionic and nonionic surfactants, cationic, ampholytic, and amphoteric surfactants can be used in the antimicrobial compositions.

Ampholytic surfactants can be broadly described as derivatives of secondary and tertiary amines having aliphatic radicals that are straight chain or branched, and wherein one of the aliphatic substituents contains from about 8 to 18 carbon atoms and at least one of the aliphatic substituents contains an anionic water-solubilizing group, e.g., carboxy, sulfonate, or sulfate. Examples of compounds falling within this description are sodium 3-(dodecylamino)propionate, sodium 3-(dodecylamino)-propane-1-sulfonate, sodium 2-(dodecylamino)ethyl sulfate, sodium 2-(dimethylamino) octadecanoate, di-sodium 3-(N-carboxymethyl-dodecylamino)propane-1-sulfonate, disodium octadecyliminodiacetate, sodium 1-carboxymethyl-2-undecylimidazole, and sodium N,N-bis(2-hydroxyethyl)-2-sulfato-3-dodecoxypropylamine.

More particularly, one class of ampholytic surfactants include sarcosinates and taurates having the general structural formula

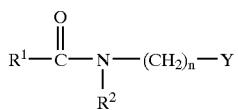

wherein $R^1$ is $C_{11}$ through $C_{21}$ alkyl, $R^2$ is hydrogen or $C_1$-$C_2$ alkyl, Y is $CO_2M$ or $SO_3M$, M is an alkali metal, and n is a number 1 through 3.

Another class of ampholytic surfactants is the amide sulfosuccinates having the structural formula

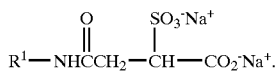

The following classes of ampholytic surfactants also can be used:

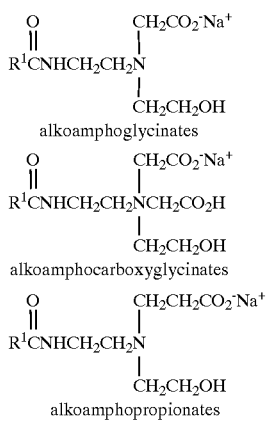

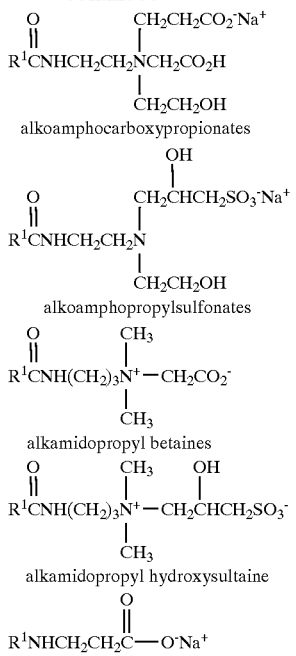

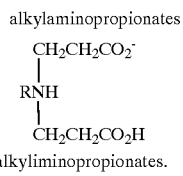

alkyliminopropionates.

Additional classes of ampholytic surfactants include the phosphobetaines and the phosphitaines.

Specific, nonlimiting examples of ampholytic surfactants useful in the present invention are sodium coconut N-methyl taurate, sodium oleyl N-methyl taurate, sodium tall oil acid N-methyl taurate, sodium palmitoyl N-methyl taurate, cocodimethylcarboxymethylbetaine, lauryldimethylcarboxymethylbetaine, lauryldimethylcarboxyethylbetaine, cetyldimethylcarboxymethylbetaine, lauryl-bis-(2-hydroxyethyl)carboxymethylbetaine, oleyldimethylgammacarboxypropylbetaine, lauryl-bis-(2-hydroxypropyl)-carboxyethylbetaine, cocoamidodimethylpropylsultaine, stearylamidodimethylpropylsultaine, laurylamido-bis-(2-hydroxyethyl)propylsultaine, disodium oleamide PEG-2 sulfosuccinate, TEA oleamido PEG-2 sulfosuccinate, disodium oleamide MEA sulfosuccinate, disodium oleamide MIPA sulfosuccinate, disodium ricinoleamide MEA sulfosuccinate, disodium undecylenamide MEA sulfosuccinate, disodium wheat germamido MEA sulfosuccinate, disodium wheat germamido PEG-2 sulfosuccinate, disodium isostearamideo MEA sulfosuccinate, cocoamphoglycinate, cocoamphocarboxyglycinate, lauroamphoglycinate, lauroamphocarboxyglycinate, capryloamphocarboxyglycinate, cocoamphopropionate, cocoamphocarboxypropionate, lauroamphocarboxypropionate, capryloamphocarboxypropionate, dihydroxyethyl tallow glycinate, cocamido disodium 3-hydroxypropyl phosphobetaine, lauric myristic amido disodium 3-hydroxypropyl phosphobetaine, lauric myristic amido glyceryl phosphobetaine, lauric myristic amido carboxy disodium 3-hydroxypropyl phosphobetaine, cocoamido propyl mono-sodium phosphitaine, lauric myristic amido propyl monosodium phosphitaine, and mixtures thereof.

The surfactant also can be a cationic alkamine oxide surfactant. An alkamine oxide useful in the present invention contains at least one long hydrocarbon chain containing at least eight carbon atoms. One class of amine oxides is the alkyl di-(lower alkyl) amine oxides, wherein the alkyl group contains 8 to 22, and preferably about 10 to about 16, carbon atoms, and can be straight or branched chain, saturated or unsaturated. The lower alkyl groups contain 1 to 7 carbon atoms, and typically are methyl. Specific examples include, but are not limited to, lauryl dimethyl amine oxide, myristyl dimethyl amine oxide, dimethyl cocoamine oxide, dimethyl (hydrogenated tallow)amine oxide, myristyl/palmityl dimethyl amine oxide, myristyl/lauryl dimethyl amine oxide, cetyl dimethyl amine oxide, stearyl dimethyl amine oxide, and myristyl/cetyl dimethyl amine oxide. These alkamine oxides have a general structural formula

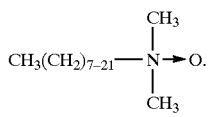

Another class of useful amine oxides includes alkyl di(hydroxy lower alkyl)amine oxides in which the alkyl group contains 8 to 22, and preferably about 10 to about 16 carbon atoms, and can be straight or branched chain, saturated or unsaturated. Specific examples, include, but are not limited to, bis(2-hydroxyethyl)cocoamine oxide, bis-(2-hydroxyethyl)tallow amine oxide, and bis(2-hydroxyethyl)stearylamine oxide. These alkamine oxides have a general structural formula

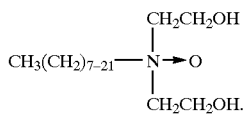

Additional useful amine oxides are termed alkamidopropyl di(lower alkyl)amine oxides in which the alkyl group contains 8 to 22, and preferably about 10 to about 16 carbon atoms, and can be straight or branched chain, saturated or unsaturated. Examples are cocoamidopropyl dimethyl amine oxide and tallowamidopropyl dimethyl amine oxide. These alkamine oxides have a general structural formula

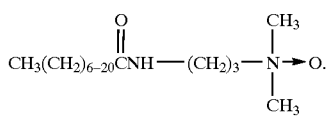

Further useful amine oxides are termed alkylmorpholine oxides in which the alkyl group contains 8 to 22, and preferably about 10 to about 16, carbon atoms, and can be straight or branched chain, saturated or unsaturated. Alkamine oxides are commercially available, for example, from Stepan Co., Northfield, Ill., and Lonza Inc., Fairlawn, N.J.

The above classes of alkamine oxide surfactants contain a $C_1$–$C_{22}$alkyl group selected from, for example, octyl, decyl, undecyl, lauryl, tri-decyl, myristyl, cetyl, stearyl, isostearyl, oleyl, and mixtures thereof. Examples of amine oxide surfactants include, but are not limited to, decyl dimethylamine oxide, lauryl dimethylamine oxide, stearyl dimethylamine oxide, oleyl dimethylamine oxide, coco dihydroxyethylamine oxide, cetyl N,N-dihydroxyethyl amine oxide, oleyl N,N-dihydroxyethylamine oxide, cocamine oxide, cocamidopropylamine oxide, lauramidopropylamine oxide, oleamine oxide, oleamidopropylamine oxide, wheat germamidopropylamine oxide, isostearamidopropylamine oxide, stearamine oxide, stearamidopropylamine oxide, cocomorpholine oxide, decylamine oxide, dihydroxyethyl $C_8$–$C_{10}$-alkoxypropylamine oxide, dihydroxyethyl $C_9$–$C_{11}$alkoxypropylamine oxide, dihydroxyethyl $C_{12}$–$C_{15}$alkoxypropylamine oxide, dihydroxyethyl cocamine oxide; dihydroxyethyl stearamine oxide, dihydroxyethyl tallowamine oxide, hydrogenated tallow amine oxide, hydroxyethyl hydroxypropyl $C_{12}$–$C_{15}$alkoxypropylamine oxide, isostearamidopropyl morpholine oxide, myristamidopropylamine oxide, myristamine oxide, palmitamidopropylamine oxide, palmitamine oxide, PEG-3 lauramine oxide, tallow amidopropylamine oxide, tallow amine oxide, undecylenamidopropylamine oxide, and mixtures thereof. Preferred alkamine oxide surfactants are the alkyl di(lower alkyl)amine oxides in which the alkyl group contains about 12 to about 16 carbon atoms, including lauramine oxide, myristamine oxide, cocamine oxide, cetamine oxide, and mixtures thereof. Most preferably, the alkamine oxide surfactant comprises lauramine oxide.

Additional cationic surfactants include a quaternary surfactant having a structural formula

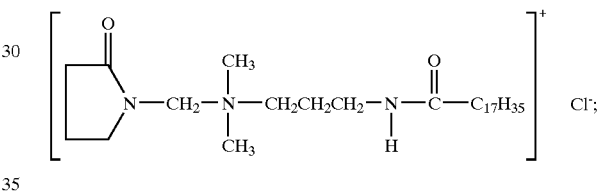

a quaternized phosphate ester, such as PHOSPHOLIPID SV, available from Mona Industries, Paterson, N.J., e.g., stearamidopropyl phosphatidyl PG-dimonium chloride, linoleamidopropyl phosphatidyl PG-dimonium chloride, coco phosphatidyl PG-dimonium chloride, cocamidopropyl phosphatidyl PG-dimonium chloride, borageamidopropyl phosphatidyl PG-dimonium chloride, and cocohydroxyethyl phosphatidyl PG-imidazolinium chloride; and other quaternized phosphate esters disclosed in Mayhew et al. U.S. Pat. No. 4,209,449. Additional quaternary ammonium surfactants can be found in the CTFA Handbook at pages 40–42, incorporated herein by reference.

C. Hydric Solvent and Hydrotrope

The present invention also contains about 1% to about 25%, by weight, of a hydric solvent, and 1% to about 40%, by weight, of a hydrotrope.

Preferred embodiments contain about 2% to about 20%, by weight, of a hydric solvent and about 2% to about 25%, by weight, of a hydrotrope. Most preferred embodiments contain about 5% to about 15%, by weight, of a hydric solvent and about 5% to about 20%, by weight, of a hydrotrope.

As defined herein, the term "hydric solvent" is a water-soluble organic compound containing one to six, and typically one to three, hydroxyl groups. The term "hydric solvent," therefore, encompasses water-soluble alcohols and diols. Specific examples of hydric solvents include, but are not limited to, methanol, ethanol, isopropyl alcohol, n-butanol, n-propyl alcohol, ethylene glycol, propylene glycol, diethylene glycol, dipropylene glycol, tripropylene glycol, hexylene glycol, butylene glycol, PEG-4, and similar hydroxyl-containing compounds.

A hydrotrope is a compound that has the ability to enhance the water solubility of other compounds. A hydrotrope utilized in the present invention lacks surfactant properties, and typically is a short-chain alkyl aryl sulfonate. Specific examples of hydrotropes includes, but are not limited to, sodium cumene sulfonate, ammonium cumene sulfonate, ammonium xylene sulfonate, potassium toluene sulfonate, sodium toluene sulfonate, sodium xylene sulfonate, toluene sulfonic acid, and xylene sulfonic acid. Other useful hydrotropes include sodium polynaphthalene sulfonate, sodium polystyrene sulfonate, sodium methyl naphthalene sulfonate, and disodium succinate.

D. Skin Care Agent

An antibacterial composition of the present invention also can contain 0% to about 5%, and preferably 0.1% to about 3%, by weight, of a skin care agent. To achieve the full advantage of the present invention, the composition contains about 0.2% to about 2.5%, by weight, of a skin care agent.

The identity of the skin care agent is not particularly limited, as long as the agent does not adversely affect the stability or efficacy of the composition. One important class of skin care agents is emollients. Emollients are cosmetic ingredients that help to maintain a soft, smooth, and pliable skin appearance. Emollients function by remaining on the skin surface or in the stratum corneum to act as lubricants, to reduce flaking, and to improve skin appearance.

In general, the skin care agent includes polymers (e.g., polyvinylpyrrolidine), protein derivatives (e.g., derivatized hydrolyzed wheat protein), ethoxylated fatty ethers, cellulosics (e.g., hydroxyethylcellulose), and similar skin care agents. For example, suitable skin care agents include, but are not limited to, esters comprising an aliphatic alcohol having 2 to about 18 carbon atoms condensed with an aliphatic or aromatic carboxylic acid including 8 to about 20 carbon atoms, e.g., isopropyl myristate, decyl oleate, and cetearyl isononanate. The ester is either straight chained or branched. Preferably, the ester has a molecular weight of less than about 500 and provides emollient properties.

Nonlimiting examples of other skin care agents include, but are not limited to, polyvinyl-pyrrolidone, polyquaternium-4, polyquaternium-7, polyquaternium-10, guar gum derivatives, hydroxypropylmethylcellulose, hydroxyethylcellulose, a polyethylene glycol, a methyl ether of a polyethylene glycol, quaternium-79, wheat germamidopropyl hydroxypropyl dimonium hydrolyzed wheat protein, stearyl methicone, dimethicone copolyol, dimethicone propyl PG betaine, poly(sodium styrene sulfonate), sorbitan oleate, steareth-2, steareth-21, isoceteth-20, PEG-7 glyceryl cocoate, PEG-75 lanolin, glycereth-26, PPG-5-ceteth-20, a $C_{12}$–$C_{20}$ alcohol, canola oil, glyceryl laurate, triglyceryl monostearate, glyceryl monostearate, vitamin E acetate, sunflower seed amidopropylethyldimonium ethylsulfate, sodium PEG-7 olive oil carboxylate, PPG-1 hydroxyethyl caprylamide, PPG-2 hydroxyethyl cocamide, mineral oil, petrolatum, aloe barbadensis, isostearamidopropylmorpholine lactate, strontium acetate, and palmitamidopropyltrimonium chloride. Additional skin care agents are listed in Appendix A. The above skin care agents can be used alone or in admixture.

E. Foam Stabilizer

An antibacterial composition of the present invention also can contain 0% to about 2%, and preferably about 0.05% to about 1.5%, by weight, of a foam stabilizer. To achieve the full advantage of the present invention, the composition contains about 0.1% to about 1%, by weight, of the foam stabilizer.

The identity of the foam stabilizer is not particularly limited, as long as the stabilizer does not adversely affect the stability and efficacy of the composition. Preferred foam stabilizers are $C_{10}$–$C_{22}$ fatty alcohols (e.g., cetyl alcohol) and $C_{10}$–$C_{22}$ fatty acids (e.g., stearic acid). Nonlimiting examples of foam stabilizers include, but are not limited to, behenyl alcohol, $C_{9-11}$ alcohols, $C_{12-13}$ alcohols, $C_{12-15}$ alcohols, $C_{12-16}$ alcohols, $C_{14-15}$ alcohols, capyrlic alcohol, arachidic acid, arachidonic acid, coconut acid, corn acid, cottonseed acid, hydrogenated coconut acid, hydrogenated menhaden acid, hydrogenated tallow acid, hydroxystearic acid, isostearic acid, cetearyl alcohol, cetyl alcohol, coconut alcohol, decyl alcohol, isocetyl alcohol, isostearyl alcohol, lauryl alcohol, behenic acid, capric acid, lauric acid, linoleic acid, linolenic acid, linseed acid, myristic acid, oleic acid, palmitic acid, pelargonic acid, octyldodecanol, undecylenyl alcohol, undecylpentadecanol, myristyl alcohol, oleyl alcohol, palm kernel alcohol, stearyl alcohol, tallow alcohol, tridecyl alcohol, caproic acid, caprylic acid, ricinoleic acid, soy acid, stearic acid, tall oil acid, tallow acid, undecanoic acid, undecylenic acid, and mixtures thereof.

F. Humectant

An antibacterial composition of the present invention also can contain 0% to about 2%, and preferably about 0.1% to about 3%, by weight, of a humectant. To achieve the full advantage of the present invention, the composition contains about 0.15% to about 2%, of a humectant.

The identity of the humectant is not particularly limited as long as the humectant does not adversely affect the stability and efficacy of the composition. A humectant typically is a water-soluble compound of low volatility, and containing a plurality (i.e., two or more) hydroxyl groups. Nonlimiting examples of humectants, include, but are not limited to, ascorbic acid, ascorbyl dipalmitate, acetamide MEA, glucose glutamate, glucuronic acid, TEA-lactate, TEA-PCA, corn syrup, fructose, glucose, glycerin, glycol, 1,2,6-hexanetriol, sodium lactate, sodium PCA, hydrogenated starch hydrolysate, inositol, lactic acid, lactose, mannitol, PCA, PEG-10 propylene glycol, polyamino sugar condensate, propylene glycol, pyridoxine dilaurate, saccharide hydrolysate, hydroxystearyl methylglucamine, glucamine, maltitol, mannitol, methyl gluceth-10, methyl gluceth-20, riboflavin, PEG-4, PEG-6, PEG-8, PEG-9, PEG-10, PEG-12, PEG-14, PEG-16, PEG-18, PEG-20, PEG-32, PEG-40, glutamic acid, glycereth-7, glycereth-12, glycereth-26, saccharide isomerate, sorbeth-20, sorbitol, sucrose, thioglycerin, tris-(hydroxymethyl)nitromethane, tromethamine, histidine, PEG-75, PEG-135, PEG-150, PEG-200, PEG-5 pentaerythritol ether, polyglyceryl sorbitol, sorbitol, urea, xylitol, and mixtures thereof.

G. Carrier

The carrier of the composition comprises water.

H. Optional Ingredients

An antibacterial composition of the present invention also can contain optional ingredients well known to persons skilled in the art, such as dyes and fragrances, that are present in a sufficient amount to perform their intended function and do not adversely affect the antibacterial efficacy of the composition. Such optional ingredients typically are present, individually, from 0% to about 5%, by weight, of the composition, and, collectively, from 0% to about 20%, by weight, of the composition.

Classes of optional ingredients include, but are not limited to, dyes, fragrances, pH adjusters, preservatives, thickeners, viscosity modifiers, buffering agents, antioxidants, foam enhancers, chelating agents, opacifiers, and similar classes of optional ingredients known to persons skilled in the art.

Specific classes of optional ingredients include alkanolamides as foam boosters; parabens as preservatives; inorganic phosphates, sulfates, and carbonates as buffering agents; EDTA and phosphates as chelating agents; and acids and bases as pH adjusters.

Examples of preferred classes of basic pH adjusters are ammonia; mono-, di-, and tri-alkyl amines; mono-, di-, and tri-alkanolamines; alkali metal and alkaline earth metal hydroxides; and mixtures thereof. However, the identity of the basic pH adjuster is not limited, and any basic pH adjuster known in the art can be used. Specific, nonlimiting examples of basic pH adjusters are ammonia; sodium, potassium, and lithium hydroxide; monoethanolamine; triethylamine; isopropanolamine; diethanolamine; and triethanolamine.

Examples of preferred classes of acidic pH adjusters are the mineral acids and polycarboxylic acids. Nonlimiting examples of mineral acids are hydrochloric acid, nitric acid, phosphoric acid, and sulfuric acid. Nonlimiting examples of polycarboxylic acids are citric acid, glycolic acid, and lactic acid. The identity of the acidic pH adjuster is not limited and any acidic pH adjuster known in the art, alone or in combination, can be used.

An alkanolamide to provide foam enhancement can be, but is not limited to, cocamide MEA, cocamide DEA, soyamide DEA, lauramide DEA, oleamide MIPA, stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA, and mixtures thereof.

A present antibacterial composition also can contain a preservative in an amount of 0% to about 0.5% by weight. Examples of preservatives include, but are not limited to, sorbic acid, potassium sorbate, the parabens (like benzylparaben), imidazolinylurea, methylchloroisothiazolinone, and the hydantoins, like DMDM hydantoin. Additional preservatives as disclosed in the *CTFA Handbook* at page 78, incorporated herein by reference.

A present antibacterial composition further can contain an antioxidant and/or an ultra-violet light (UV) absorber, each independently in an amount of 0% to about 0.5% by weight. Examples of antioxidants of UW absorbers include, but are not limited to, BHA, BHT, sodium ascorbate, potassium sulfite, erythorbic acid, benzophenone-1 through benzophenone-12, and PABA. Additional antioxidants and UV absorbers can be found in the *CTFA Handbook* at pages 78 and 98, incorporated herein by reference.

In addition, the antibacterial compositions of the present invention do not rely upon a low pH or a high pH to provide a rapid reduction in bacterial populations. Antibacterial compositions of the present invention can have a pH of about 4 to about 9, but at the two extremes of this pH range, the compositions can be irritating to the skin or damaging to other surfaces contacted by the composition. Accordingly, antibacterial compositions of the present invention preferably have a pH of about 5 to about 8, and more preferably about 6 to about 8. To achieve the full advantage of the present invention, the antibacterial compositions have a pH of about 6.5 to about 7.5.

To demonstrate the new and unexpected results provided by the antibacterial compositions of the present invention, the examples in Appendix A were prepared, and the ability of the compositions to control Gram positive and Gram negative bacteria was determined. The weight percentage listed in each of the examples represents the actual, or active, weight amount of each ingredient present in the composition. The compositions were prepared by blending the ingredients, as understood by those skilled in the art.

The following materials were used as ingredients in the examples. The source of each ingredient and its abbreviation are summarized below:

| Chemical Name | Trade Name | Supplier | Abbreviation |
|---|---|---|---|
| Surfactants | | | |
| Ammonium Lauryl Sulfate | STANDAPOL A (28.3% active) | Cognis Corporation Ambler, PA | ALS |
| Sodium Lauryl Ether Sulfate (2-mole) | STANDAPOL ES-2 (25.71% active) | Cognis Corporation | SLES2 |
| Ammonium Cocyl Isethionate | JORDAPON ACI-30G Isethionate (25% active) | BASF Corporation Mount Olive, NJ | ACI |
| Cocamidopropyl-betaine | MACKAM 35-HP (about 30% active) | McIntyre Group Chicago, IL | CAPB |
| Hydrotropes | | | |
| Sodium Xylene Sulfonate | STEPANATE SXS (40–42% active) | Stepan Company Northfield, IL | SXS |
| Hydric Solvents | | | |
| Dipropylene Glycol | Dipropylene Glycol (100% active) | Ashland Chemical Co. Covington, KY | DPG |
| Polymers | | | |
| Polyvinylpyrrolidone | PVP K-15 (98–99% active) | International Specialty Products Wayne, NJ | PVPK15 |
| Polyvinylpyrrolidone | PVP K-30 (98–99% active) | International Specialty Products | PVPK30 |
| Guar Gum, 2-Hydroxy-3-(Trimethylammonio)-Propyl Ether Chloride | JAGUAR C13S (88–94% active) | Rhodia Cranbury, NJ | JAGC13S |
| Guar Gum, 2-Hydroxy-3-(Trimethylammonio)-Propyl Ether Chloride | JAGUAR C14S (88–94% active) | Rhodia | JAGC14S |
| Guar Gum, 2-Hydroxy-3-(Trimethylammonio)-Propyl Ether Chloride | JAGUAR C162 (91% active) | Rhodia | JAGC162 |
| Guar Gum, 2-Hydroxypropyl Ether | JAGUAR HP8 (88–94% active) | Rhodia | JAGHP8 |
| Guar Gum, 2-Hydroxypropyl Ether | JAGUAR HP60 (87–94% active) | Rhodia | JAGHP60 |
| Guar Gum, 2-Hydroxypropyl Ether | JAGUAR HP105 (90–97% active) | Rhodia | JAGHP105 |
| Guar Gum, 2-Hydroxypropyl Ether | JAGUAR HP120 (91–95% active) | Rhodia | JAGHP120 |
| Polyquaternium-7 | MERQUAT 550 (9% active) | Calgon Corporation Pittsburgh, PA | MQ550 |
| Polyquaternium-4 | CELQUAT SC-230M (100% active) | National Starch & Chemical Bridgewater, NJ | CQSC230M |
| Polyquaternium-10 | CELQUAT SC-240C (100% active) | National Starch & Chemical | CQSC240C |

-continued

| Chemical Name | Trade Name | Supplier | Abbreviation |
|---|---|---|---|
| Polyquaternium-4 | CELQUAT H-100 (100% active) | National Starch & Chemical | CQH100 |
| Hydroxypropylmethylcellulose | METHOCEL 40–100 (90–95% active) | Dow Chemical Co. Midland, MI | MCL40100 |
| Hydroxyethylcellulose | NATROSOL 250 HHR (95–100% active) | Aqualon/ Hercules Wilmington, DE | NATSOL250HHR |
| PEG-6 & PEG-32 | CARBOWAX Sentry Polyethylene Glycol 540 (100% active) | Dow Chemical Co. Midland, MI | CWAX540 |
| PEG-18 | CARBOWAX Sentry Polyethylene Glycol 900 (100% active) | Dow Chemical Co. | CWAX900 |
| MethoxyPEG-1000 | CARBOWAX Methoxypolyethylene glycol 5000 (100% active) | Dow Chemical Co. | MET5000 |
| MethoxyPEG-40 | CARBOWAX Methoxypolyethyleneglycol 2000 (100% active) | Dow Chemical Co. | MET2000 |
| PEG-100 | CARBOWAX Polyethyleneglycol 4600 (100% active) | Dow Chemical Co. | PG4600 |
| PEG-6ME | PEG6ME (100% active) | Dow Chemical Co. | PEG6ME |
| PEG-45M | POLYOX WSR-N-60 (100% active) | Amerchol Institute, WV | WSRN60 |
| PEG-14M | POLYOX WSR-205 (100% active) | Amerchol | WSR205 |
| PEG-14M | POLYOX WSR-N-3000 (99% active) | Amerchol | WSR-N-3000 |
| Poly(sodium styrene sulfonate) | FLEXAN 130 (30% active) | National Starch & Chemical | FLEX130 |
| Protein Derivatives | | | |
| Wheatgermamidopropyl Hydroxypropyl Dimonium Hydrolyzed Wheat Protein | MACKPRO WWP (35% active) | McIntyre Group | WWP |
| Quaternium-79 Hydrolyzed Wheat Protein | MACKPRO NLW (33% active) | McIntyre Group | NLW |
| Silicone Derivatives | | | |
| Dimethicone Propyl PG Betaine | ABIL B 9950 (29–31% active) | Goldschmidt Hopewell, VA | DIMETHPGB |
| Stearyl Methicone | SILCARE 41M30 (88% active) | Clariant Gainesville, FL | STMETH |
| Dimethicone Copolyol | Dow Corning 193 (100% active) | Dow Corning Auburn, MI | DC193 |
| Humectants | | | |
| Glycerine | Glycerin, USP (100% active) | Cognis/Emery Cincinnati, OH | GLY |
| Sodium PCA | AJIDEW NL-50 (50% active) | Ajinomoto Teaneck, NJ | NaPCA |

-continued

| Chemical Name | Trade Name | Supplier | Abbreviation |
|---|---|---|---|
| Steareth-2 | Polyoxyethylene-(2) stearyl ether (BRIJ 72) (99% active) | ICI Americas Bridgewater, NJ | BRIJ72 |
| Steareth-21 | Polyoxyethylene-(21) stearyl ether (BRIJ 721) (99% active) | ICI Americas | BRIJ721 |
| Isoceteth-20 | ARLASOLVE 200 (73% active) | ICI Americas | ARL200 |
| PEG-7 Glyceryl Cocoate | CETIOL HE (100% active) | Cognis Corporation | PEG7GC |
| PEG-75 Lanolin | FANCOR LAN AQUA 501 (100% active) | Fanning Corporation Chicago, IL | PEG75LAN |
| Sorbitan Oleate | ARLACEL 80 (100% active) | ICI Americas | ARL80 |
| Cocoglucoside and Glyceryl Oleate | LAMESOFT PO-65 (65% active) | Cognis Corporation | LMSFT |
| Glycereth-26 | JEECHEM GL-26 (100% active) | Jeen International Corp. Little Falls, NJ | |
| PPG-5-Ceteth-20 | PROCETYL AWS (100% active) | Croda Parsippany, NJ | PPG5CET20 |
| Long-chain Fatty Materials | | | |
| Cetyl alcohol | Cetyl alcohol (100% active) | Aldrich Milwaukee, WI | CETOH |
| Cetearyl alcohol | STENOL 1618 (100% active) | Cognis Corporation | CETEAROH |
| Stearic Acid | Stearic Acid (100% active) | Aldrich | StAC |
| Isopropyl Myristate | KESSCO IPM (100% active) | Stepan Company | IPM |
| Decyl Oleate | CETIOL V (100% active) | Cognis Corporation | DCYLOL |
| Cetearyl Isononanate | CETIOL SN (100% active) | Cognis Corporation | CETISONON |
| Lipid-like Materials | | | |
| Canola Oil | Canola Oil (100% active) | Procter & Gamble Cincinnati, OH | CANOL |
| Glyceryl Laurate | LAURICIDIN (100% active) | Med-Chem Labs, Inc. Galena, IL | LRCDN |
| Triglyceryl Monostearate | | | TGMS |
| Glyceryl Monostearate | EMEREST 2400 (100% active) | Cognis Corporation | GMS |
| Other Materials | | | |
| Mackalene 1216 | MACKERNIUM 1216 (24% active) | McIntyre Group | MAC1216 |
| Sunflower seed amidopropylethyldimonium ethylsulfate | MACKERNIUM SFES (80% active) | McIntyre Group | SFES |
| Sodium PEG-7 Olive Oil Carboxylate | OLIVEM 400 (35% active) | B&T Milano, IT | OL400 |
| Vitamin E Acetate | Vitamin E Acetate (100% active) | Roche Nutley, NJ | VitEAc |
| PPG-1 Hydroxyethyl Caprylamide | PROMIDIUM CC (100% active) | Uniquema Paterson, NJ | PCC |
| PPG-2 | PROMIDIUM | Uniquema | PCO |

-continued

| Chemical Name | Trade Name | Supplier | Abbreviation |
|---|---|---|---|
| Hydroxyethyl Cocamide | CO (100% active) | | |
| Mineral Oil | Mineral Oil (100% active) | Mallinckradt Hazelwood, MO | MO |
| Petrolatum | | | PETR |
| Aloe Barbadensis Leaf Juice | ACTIVERA 104 (≦1% active) | Active Organics Lewisville, TX | ALOE |
| Isostearamidopropylmorpholine Lactate | MACKALENE 426 (25% active) | McIntyre Group | ISML |
| Strontium Acetate | Sr(OAc)$_2$ (100% active) | Aldrich | Sr(OAc)$_2$ |
| Palmitamidopropyltrimonium Chloride | VARISOFT PATC (57–61% active) | Goldschmidt | VRSFT |
| Antimicrobial Agent | | | |
| Triclosan | IRGASAN DP-300 (100% active) | Ciba Specialty Chemicals Corp. Greensboro, NC | TCS |

The following methods were used in the preparation and testing of the examples:

a) Determination of Rapid Germicidal (Time Kill) Activity of Antibacterial Products. The activity of antibacterial compositions was measured by the time-kill method, whereby the survival of challenged organisms exposed to an antibacterial test composition is determined as a function of time. In this test, a diluted aliquot of the composition is brought into contact with a known population of test bacteria for a specified time period at a specified temperature. The test composition is neutralized at the end of the time period, which arrests the antibacterial activity of the composition. The percent or, alternatively, log reduction from the original bacterial population is calculated. In general, the time kill method is known to those skilled in the art.

The composition can be tested at any concentration from 0–100%. The choice of which concentration to use is at the discretion of the investigator, and suitable concentrations are readily determined by those skilled in the art. For example, viscous samples usually are tested at 50% dilution, whereas nonviscous samples are not diluted. The test sample is placed in a sterile 250 mL beaker equipped with a magnetic stirring bar, and the sample volume is brought to 100 mL, if needed, with sterile, deionized water. All testing is performed in triplicate, the results are combined, and the average log reduction is reported.

The choice of contact time period also is at the discretion of the investigator. Any contact time period can be chosen. Typical contact times range from 15 seconds to 5 minutes, with 30 seconds and 1 minute being typical contact times. The contact temperature also can be any temperature, typically room temperature, or about 25 degrees Celsius.

The bacterial suspension, or test inoculum, is prepared by growing a bacterial culture on any appropriate solid media (e.g., agar). The bacterial population then is washed from the agar with sterile physiological saline, and the population of the bacterial suspension is adjusted to about 10⁸ colony forming units per mL (cfu/mL).

The table below lists the test bacterial cultures used in the following tests and includes the name of the bacteria, the ATCC (American Type Culture Collection) identification number, and the abbreviation of the name of the organism used hereafter.

| Organism Name | ATCC # | Abbreviation |
|---|---|---|
| Staphylococcus aureus | 6538 | Sa |
| Escherichia coli | 11229 | Ec |
| Serratia marcescens | 14756 | Sm |
| Klebsiella pneumoniae | 10031 | Kp |

Staphylococcus aureus is a Gram positive bacteria, whereas Escherichia coli and Serratia marcescens are Gram negative bacteria. Many formulations were screened for antibacterial efficacy using Serratia marcescens because Sm is relatively difficult to kill rapidly and is used as a test organism in the "Health Care Personnel Hand wash Test" described in "21 CFR Parts 333 and 369 Tentative Final Monograph for Heath Care Antiseptic Drug Products; Proposed Rule" (Food and Drug Administration, *Federal Register*, Vol. 59, No. 116, Friday, Jun. 17, 1994 Proposed Rules).

The beaker containing the test composition is placed in a water bath (if constant temperature is desired), or placed on a magnetic stirrer (if ambient laboratory temperature is desired). The sample then is inoculated with 1.0 mL of the test bacterial suspension. The inoculum is stirred with the test composition for the predetermined contact time. When the contact time expires, 1.0 mL of the test composition/bacteria mixture is transferred into 9.0 mL of Tryptone-Histidine-Tween Neutralizer Solution (THT). Decimal dilutions to a countable range then are made. The dilutions can differ for different organisms. Selected dilutions are plated in triplicate on TSA+ plates (TSA+ if Trypticase Soy Agar with Lecithin and Polysorbate 80). The plates then are incubated for 25±2 hours, and the colonies are counted for the number of survivors, and the percent or log reduction is calculated. The control count (numbers control) is determined by conducting the procedure as described above with the exception that THT is used in place of the test composition. The plate counts are converted to cfu/mL for the numbers control and samples, respectively, by standard microbiological methods. The log reduction is calculated using the formula Log reduction=Log$_{10}$(numbers control)–log$_{10}$(test sample survivors).

The following table correlates percent reduction in bacterial population to log reduction.

| % Reduction | Log Reduction |
|---|---|
| 90 | 1 |
| 99 | 2 |
| 99.9 | 3 |
| 99.99 | 4 |
| 99.999 | 5 | b) Physical Stability Screening. The stability of test compositions was determined by observing the compositions several days after preparation to determine whether phase separation occurred. This screening test was used to determine whether the test composition would be tested further.

c) Foam Property Screening. The foam properties and end use performance enhancement of the compositions was determined by the following two methods:

1) Bottle Shake Foam Test. This test was performed by inverting bottles containing test compositions and timing the persistence of the foam head. In a typical test, eight to ten compositions (each contained in a capped, 1L, French square bottle) are tested as a set. Each set includes a control which has the same base formula as the others, but does not contain any performance-enhancing additives. The set of samples first is allowed to equilibrate at a common temperature (usually about 25° C.). The bottles then are arranged in a row and inverted five times each, all within about 1 minute. The bottles then are allowed to stand for about 1 to 3 hours, and the time of foam collapse (as judged by an opening in the foam head equal to about 2.5 cm) is recorded. The foam collapse times are compared to the control and summarized as shown in the table below:

| Foam Rating (Bottle or Pump Test) | Description |
| --- | --- |
| + + + | Bottle Foam stable for several days |
| + + | Foam persisted longer than the test time |
| + | Foam persisted longer than control sample, but less than total test time |
| 0 | Foam collapsed at the same time as control |
| − | Foam collapsed sooner than control |
| − − | Foam collapsed almost immediately |
| NT | Not tested |

2) Pump Foam Test. Because a preferred route of application is use of a self-foaming pump, this test assesses stability of test sample foam ejected from this type of pump. The self-foaming pump used in this test is manufactured by Air-spray International B.V., Alkmaar, Holland (model Airspray 1.65 ml TT Pump with EVA(PIB) liner). This test was performed by ejecting one pump stroke of foam on a precleaned watch glass (100 mm, Corning Glass Works, #9985) and observing the time of foam collapse. In a typical test, 8 to 10 samples (each contained in a plastic bottle equipped with a foaming pump) are tested as a set. As in the Bottle Foam Test, each set includes a control which has the same base formula as the others, but does not contain any performance-enhancing additives. The set of samples first is allowed to equilibrate at a common temperature (usually about 25° C.). The pumps/bottles and corresponding watch glasses are arranged in two parallel rows. The pumps are primed with three strokes just prior to the test. One pump-stroke of foam is ejected onto the corresponding watch glass of each sample, all within about 1 minute. The foam samples then are allowed to stand for about 1 to 3 hours, and the time of foam collapse (as judged by circle of bubbles about 5 mm or less) is recorded. The foam collapse times are compared to the control and summarized as shown in the table above.

d) Preparation of Samples. The preparation of all samples involved equipment and procedures normally employed in formula development laboratories. All percents were by weight based on the active level of each ingredient.

e) Summary formula descriptions in example tables. A typical table entry for a test composition is "0.6TCS/5DPG/15SXS/1.5ALS/0.5CAPB/0.2-PVPKS15." This entry is defined as 0.6% triclosan (TCS), 5% dipropylene glycol (DPG), 15% sodium xylene sulfonate (SXS), 1.5% ammonium lauryl sulfate (ALS), 0.5% cocamidopropyl betaine (CAPB), 0.2% polyvinylpyrrolidone polymer (PVP K-15), and the remainder of the formula is water (typically with 0.2%, by total weight, of a citrate/phosphate buffer designed to provide a pH of about 6).

f) Preparation of saturated solutions of TCS in water. A four-liter flask was equipped with a 3-inch magnetic stir bar and charged with approximately 7.5 grams (g) TCS and 3 liters (L) of water. The flask then was placed in a water bath, stirred, and heated (40–45° C.) for at least 8 hours. The flask containing the resulting TCS/water suspension was removed from the water bath, and the warm suspension filtered through a Coors #32-H porcelain Buchner funnel equipped with Whatman #40 (5.5 cm) filter paper. The filtering assembly was attached to a two-liter vacuum filter flask, and filtration was conducted in batches. The filtrate then was transferred to another four-liter flask and allowed to cool. Typically, fine needles of TCS crystals formed after the filtrate was stored at room temperature for a few days.

For some time-kill studies, the TCS solution was refiltered at room temperature before use in the study. For other time-kill studies, a small amount of crystalline TCS was allowed to remain in the test container to ensure saturation in the event of a temperature change. It was assumed that TCS crystals present in the time-kill test vessel would not affect test results because crystalline TCS is unavailable to act on the bacteria (i.e., is not solubilized).

To determine the concentration of TCS in the water solutions, filtered samples (in triplicate) were analyzed by HPLC. The apparatus used to filter the solutions was a Whatman AUTOVIAL®, with 0.45 $\mu$m PTFE membrane and glass microfiber prefilter, cat. No. AV125UORG. TCS concentrations were calculated using a linear regression line fit (Microsoft EXCEL® software) to TCS/IPA standards included on the same HPLC run.

The following examples demonstrate that the new and unexpected results achieved by the present invention are attributed (in part) to a selection of esthetic enhancing and skin care additives which maintain a phase-stable system, do not hinder antibacterial activity, and contribute to composition performance and esthetics.

EXAMPLE 1A

Phase stability and foam performance attributed to polyvinylpyrrolidone (PVP) polymer additives—The compositions in this example demonstrate the phase stability and performance observed during testing of compositions containing PVP polymer additives. In this test, PVP K-15 failed to improve foam properties in the base formula evaluated, whereas PVP K-30 exhibited foam property improvement at higher surfactant levels.

| Polymers | Comment | Formula | Stable (S)/Not Stable (NS) | Bottle Foam Test | Pump Foam Test |
| --- | --- | --- | --- | --- | --- |
| PVPK15 | MW = 8,000 | 0.6TCS/5DPG/15SXS/1.5ALS/0.5CAPB/0.2PVPK15 | S | — | — |
| PVPK30 | MW = 38,000 | 0.3TCS/5DPG/15SXS/0.75ALS/0.05PVPK30 | NS | NT | NT |
| PVPK30 | MW = 38,000 | 0.3TCS/5DPG/15SXS/0.75ALS/0.02PVPK30 | NS | NT | NT |
| PVPK30 | MW = 38,000 | 1.0TCS/5DPG/15SXS/2.5ALS/0.75CAPB/0.1PVPK30 | S | ++ | ++ |

EXAMPLE 1B

Phase stability and foam performance attributed to modified guar polymer additives—The compositions in this example demonstrate the phase stability observed during testing of compositions containing modified guar polymer additives. The nonionic 2-hydroxypropyl ether guar gum polymers were successfully incorporated into the compositions. However, two moderately charged cationic polymers (JAGUAR C13S and C14S) were not stable in the base formula. JAGUAR C162, a similar polymer having less charge density, was effectively incorporated into compositions of the present invention. JAGUAR HP-60-containing compositions exhibited excellent slip properties for dry application, when the polymer is present in a sufficient amount to provide a perceivable esthetic improvement, but not an amount such that the composition is too slippery and too thick for use with a self-foaming pump.

| Polymers | Comment | Formula | Stable (S)/ Not Stable (NS) | Bottle Foam Test | Pump Foam Test |
| --- | --- | --- | --- | --- | --- |
| JAGUAR HP-8 | Guar Gum, 2-Hydroxypropyl Ether | 0.3TCS/5DPG/15SXS/0.75ALS/ 0.05HP8 | S | + | + |
| JAGUAR HP-60 | Guar Gum, 2-Hydroxypropyl Ether | 1.0TCS/5DPG/15SXS/2.5ALS/ 0.75CAPB/0.2HP60 | S | 0 | + |
| JAGUAR HP-60 | Guar Gum, 2-Hydroxypropyl Ether | 0.3TCS/5DPG/15SXS/0.75ALS/ 0.2HP60 | S | + | − |
| JAGUAR HP-60 | Guar Gum, 2-Hydroxypropyl Ether | 0.3TCS/5DPG/15SXS/0.75ALS/ 0.1HP60 | S | + | + |
| JAGUAR HP-60 | Guar Gum, 2-Hydroxypropyl Ether | 0.3TCS/5DPG/15SXS/0.75ALS/ 0.1HP60 | S | + | + |
| JAGUAR HP-60 | Guar Gum, 2-Hydroxypropyl Ether | 0.3TCS/5DPG/15SXS/0.75ALS/ 0.05HP60 | S | + | − |
| JAGUAR HP-60 | Guar Gum, 2-Hydroxypropyl Ether | 0.3TCS/5DPG/15SXS/0.75ALS/ 0.075HP60 | S | − | − |
| JAGUAR HP-105 | Guar Gum, 2-Hydroxypropyl Ether | 0.3TCS/5DPG/15SXS/0.75ALS/ 0.05HP105 | S | + | − |
| JAGUAR HP-120 | Guar Gum, 2-Hydroxypropyl Ether | 0.3TCS/5DPG/15SXS/0.75ALS/ 0.05HP120 | S | + | + |
| JAGUAR C13S | Guar Gum, 2-Hydroxy-3-(tri-methylammonio)-propyl ether chloride | 0.3TCS/5DPG/15SXS/0.75ALS/ 0.5JAGC13S | NS | NT | NT |
| JAGUAR C13S | Guar Gum, 2-Hydroxy-3-(tri-methylammonio)-propyl ether chloride | 0.3TCS/5DPG/15SXS/0.75ALS/ 0.05JAGC13S | NS | NT | NT |
| JAGUAR C13S | Guar Gum, 2-Hydroxy-3-(tri-methylammonio)-propyl ether chloride | 0.3TCS/5DPG/15SXS/0.75ALS/ 0.2JAGC13S | NS | NT | NT |
| JAGUAR C14S | Guar Gum, 2-Hydroxy-3-(tri-methylammonio)-propyl ether chloride | 0.3TCS/5DPG/15SXS/0.75ALS/ 0.5JAGC14S | NS | NT | NT |
| JAGUAR C14S | Guar Gum, 2-Hydroxy-3-(tri-methylammonio)-propyl ether chloride | 0.3TCS/5DPG/15SXS/0.75ALS/ 0.05JAGC14S | NS | NT | NT |
| JAGUAR C14S | Guar Gum, 2-Hydroxy-3-(tri-methylammonio)-propyl ether chloride | 0.3TCS/5DPG/15SXS/0.75ALS/ 0.2JAGC14S | NS | NT | NT |
| JAGUAR C162 | Guar Gum, 2-Hydroxy-3-(tri-methylammonio)-propyl ether chloride | 0.3TCS/5DPG/15SXS/0.75ALS/ 0.05C162 | S | + | − |

EXAMPLE 1C

Phase stability and foam performance attributed to a cationic copolymer containing 50% dimethyl diallyl ammonium chloride (DMAAC) and 50% acrylamide additive—The compositions in this example demonstrate the phase stability observed by incorporating a highly charged polymer into the composition. It was found that a relatively high surfactant level was required to successfully incorporate a highly charged polymer into the composition, even at a 0.05% polymer. As described in U.S. Pat. No. 6,107,261, the highest antimicrobial activity is obtained for compositions having a high % saturation of antimicrobial agent. Thus, raising the surfactant level to accommodate solubilization of the polymer or other additives, requires a higher level of antibacterial agent in the composition to maintain a high % saturation. For example, in the first composition of this example, 1.0% TCS was required to maintain the desired % saturation vs. 0.3% in compositions containing a lower amount of surfactant.

| Polymers | Comment | Formula | Stable (S)/ Not Stable (NS) | Bottle Foam Test | Pump Foam Test |
|---|---|---|---|---|---|
| MERQUAT 550 | MW = 1,600,000/- highly charged cationic copolymer | 1.0TCS/5DPG/15SXS/ 2.5ALS/0.75CAPB/0.2MQ550 | S | ++ | + |
| MERQUAT 550 | MW = 1,600,000/- highly charged cationic copolymer | 0.3TCS/5DPG/15SXS/0.75 ALS/0.05MQ550 | NS | NT | NT |
| MERQUAT 550 | MW = 1,600,000/- highly charged cationic copolymer | 0.3TCS/5DPG/15SXS/0.75 ALS/0.05MQ550 | NS | NT | NT |
| MERQUAT 550 | MW = 1,600,000/- highly charged cationic copolymer | 0.3TCS/5DPG/15SXS/0.75 ALS/0.05MQ550 | NS | NT | NT |

EXAMPLE 1D

Phase stability and foam performance attributed to cationic hydroxyethylcellulose polymer additives—CELQUAT SC-230M and SC-240C each have a hydroxyethylcellulose (HEC) backbone further derivatized with 2-hydroxy (trimethylammonio)propyl ether to provide a cationic polymer. The average molecular weight of the HEC backbone of SC-240C is about 63% that of SC-230M. The performance of these two polymers is similar except SC-230M produced a higher composition viscosity at a lower weight % level. Thus, SC-240C is preferred polymer for use with a foaming pump because of a lower viscosity, which is attributed to, but not relied upon, a lower molecular weight of this polymer compared to SC-230M.

CELQUAT H-100 has an HEC backbone which is derivatized with polyDMDAC, and has a high localized nitrogen charge density. In the present compositions, CELQUAT H-100 provides excellent foam stability, skin feel, and skin care properties.

| Polymers | Comment | Formula | Stable (S)/ Not Stable (NS) | Bottle Foam Test | Pump Foam Test |
|---|---|---|---|---|---|
| CELQUAT SC-230M | MW = 1,750,000 | 1.0TCS/5DPG/15SXS/2.5ALS/ 0.75CAPB/0.1CQSC230M | S | ++ | + |
| CELQUAT SC-230M | MW = 1,750,000 | 0.3TCS/5DPG/15SXS/0.75ALS/ 0.1CQSC230M | S | + | − |
| CELQUAT SC-230M | MW = 1,750,000 | 0.6TCS/5DPG/15SXS/1.5ALS/ 0.5CAPB/0.3CQSC230M | S | + | − |
| CELQUAT SC-230M | MW = 1,750,000 | 0.6TCS/5DPG/15SXS/1.5ALS/ 0.5CAPB/5GLY/0.5CQSC230M | S | + | + |
| CELQUAT SC-230M | MW = 1,750,000 | 0.6TCS/5DPG/15SXS/1.5ALS/ 0.75CAPB/0.5CQSC230M | S | − | ++ |
| CELQUAT SC-230M | MW = 1,750,000 | 0.6TCS/5DPG/15SXS/1.5ALS/ 0.5CAPB/5GLY/0.5CQSC230M | S | + | + |
| CELQUAT SC-240C | MW = 1,100,000 | 0.6TCS/5DPG/15SXS/1.5ALS/ 0.5CAPB/0.5CQSC240C | S | + | − |

-continued

| Polymers | Comment | Formula | Stable (S)/ Not Stable (NS) | Bottle Foam Test | Pump Foam Test |
|---|---|---|---|---|---|
| CELQUAT SC-240C | MW = 1,100,000 | 0.6TCS/5DPG/15SXS/1.5ALS/ 0.5CAPB/1.0CQSC240C | S | + | + |
| CELQUAT H-100 | MW = 1,400,000 | 0.6TCS/5DPG/15SXS/1.5ALS/ 0.75CAPB/0.5CQH100 | S | ++ | ++ |

EXAMPLE 1E

Phase stability and foam performance attributed to hydroxypropylcellulose (HPC) and hydroxyethylcellulose (HEC) polymer additives—Compositions containing the HPC polymer exhibited acceptable foam properties, but marginal phase instability, at lower surfactant levels. The composition containing the HEC polymer was phase stable, but foam properties were not improved.

| Polymers | Comment | Formula | Stable (S)/ Not Stable (NS) | Bottle Foam Test | Pump Foam Test |
|---|---|---|---|---|---|
| METHOCEL 40-100 | Hydroxypropylcellulose | 0.3TCS/5DPG/15SXS/ 0.75ALS/0.1MCL40100 | S (turbid) | + | + |
| METHOCEL 40-100 | Hydroxypropylcellulose | 0.3TCS/5DPG/15SXS/ 0.75ALS/0.2MCL40100 | NS | NT | NT |
| METHOCEL 40-100 | Hydroxypropylcellulose | 0.3TCS/5DPG/15SXS/ 0.75ALS/0.05MCL40100 | S (turbid) | + | + |
| METHOCEL 40-100 | Hydroxypropylcellulose | 1.0TCS/5DPG/15SXS/ 2.5ALS/0.75CAPB/ 0.2MCL40100 | S | ++ | + |
| NATROSOL 250 HHR | Hydroxyethylcellulose | 0.3TCS/5DPG/15SXS/ 0.75ALS/ 0.05NATSOL250HHR | S | − | − |

EXAMPLE 1F

Phase stability and foam performance attributed to polyethylene glycol (PEG) and methoxypolyethylene glycol (MPEG) polymer additives—The compositions in this example illustrate the effect of increasing polymer chain length on phase stability, i.e., longer polymer chains decrease composition stability. In addition, while shorter chain polymers provided a stable base formula, foam performance was best for the shortest chain polymer (PEG6ME).

| Polymers | Comment | Formula | Stable (S)/ Not Stable (NS) | Bottle Foam Test | Pump Foam Test |
|---|---|---|---|---|---|
| PEG6ME | MW = 335 to 365 | 0.6TCS/5DPG/15SXS/1.5 ALS/0.5CAPB/1PEG6-ME | S | ++ | − |
| CARBOWAX 540 (PEG-6 & PEG-32) | MW = 468 to 534 | 0.6TCS/5DPG/15SXS/ 1.5ALS/0.5CAPB/1.0CWA X540 | S | − | − |
| CARBOWAX 900 (PEG-18) | MW = 855 to 945 | 0.6TCS/5DPG/15SXS/ 1.5ALS/0.5CAPB/1.0CWA X900 | S | − | − |
| Methoxypolyethylene glycol 2000 (Methoxy PEG-40) | MW = 1800 to 2200 | 0.6TCS/5DPG/15SXS/ 1.5ALS/0.5CAPB/0.5MET 2000 | S | − | − |
| Polyethylene glycol 4600 (PEG-100) | MW = 4140 to 5060 | 0.6TCS/5DPG/15SXS/ 1.5ALS/0.5CAPB/0.5PG4 600 | S | − | − |
| Methoxypolyethylene glycol 5000 (Methoxy PEG 1000) | MW = 4375 to 5675 | 0.6TCS/5DPG/15SXS/ 1.5ALS/0.5CAPB/0.5MET 5000 | S | − | − |

-continued

| Polymers | Comment | Formula | Stable (S)/ Not Stable (NS) | Bottle Foam Test | Pump Foam Test |
|---|---|---|---|---|---|
| POLYOX WSR-N-3000 | MW = 400,000 | 0.6TCS/5DPG/15SXS/ 1.5ALS/0.5CAPB/1WSR-N-3000 | S (slightly turbid) | NT | NT |
| POLYOX WSR-205 | MW = 600,000 | 0.6TCS/5DPG/15SXS/ 1.5ALS/0.5CAPB/0.5WSR 205 | S (turbid) | NT | NT |
| POLYOX WSR-N-60 | MW = 2,000,000 | 0.6TCS/5DPG/15SXS/ 1.5ALS/0.5CAPB/0.05WS RN60 | NS | NT | NT |

EXAMPLE 1G

Phase stability and foam performance attributed to a poly(sodium styrene sulfonate) polymer additive—This example illustrates the performance of an anionic polymer additive. This polymer provided a stable composition, but marginal lather performance.

| Polymers | Comment | Formula | Stable (S)/ Not Stable (NS) | Bottle Foam Test | Pump Foam Test |
|---|---|---|---|---|---|
| FLEXAN 130 | | 0.6TCS/5DPG/15SXS/1.5ALS/ 0.5CAPB/1.0FLEX130 | S | – | – |

EXAMPLE 2

Phase stability and foam performance attributed to protein derivative additives—A majority of the compositions evaluated in this example were phase stable and exhibited moderate foam property enhancement. NLW was solubilized more easily by the base composition than WWP.

| Protein Derivative | Comment | Formula | Stable (S)/ Not Stable (NS) | Bottle Foam Test | Pump Foam Test |
|---|---|---|---|---|---|
| MACKPRO WWP | Wheatgermamidopropyl Hydroxypropyl Dimonium Hydrolyzed Wheat Protein | 0.3TCS/5DPG/15SXS/ 0.75ALS/0.1WWP | S | – | + |
| MACKPRO WWP | Wheatgermamidopropyl Hydroxypropyl Dimonium Hydrolyzed Wheat Protein | 1.0TCS/5DPG/15SXS/ 2.5ALS/0.75CAPB/0.2WWP | NS | NT | NT |
| MACKPRO WWP | Wheatgermamidopropyl Hydroxypropyl Dimonium Hydrolyzed Wheat Protein | 0.3TCS/5DPG/15SXS/ 0.75ALS/1.0WWP | S | + | + |
| MACKPRO WWP | Wheatgermamidopropyl Hydroxypropyl Dimonium Hydrolyzed Wheat Protein | 0.3TCS/5DPG/15SXS/ 0.75ALS/0.5WWP | S | + | + |
| MACKPRO NLW | Quaternium-79 Hydrolyzed Wheat Protein | 0.3TCS/5DPG/15SXS/ 0.75ALS/0.2NLW | S | + | – |
| MACKPRO NLW | Quaternium-79 Hydrolyzed Wheat Protein | 1.0TCS/5DPG/15SXS/ 2.5ALS/0.75CAPB/0.1NLW | S | 0 | + |
| MACKPRO NLW | Quaternium-79 Hydrolyzed Wheat Protein | 1.0TCS/5DPG/15SXS/ 2.5ALS/0.75CAPB/0.2NLW | S | + | + |

EXAMPLE 3

Phase stability and foam performance attributed to humectant additives—Two humectants, glycerin and sodium pyrrolidone carboxylate (sodium PCA), were evaluated. This example shows that phase stability is not adversely affected by these humectants, and that the amount of humectant can be adjusted for optimum foam properties.

EXAMPLE 4

Phase stability and foam performance attributed to ethoxylated additives—Ethoxylated additives provide an advantage because of a wide variety of raw materials and the ability to predetermine properties by a judicious selection of the level of ethoxylation of the additive. It was observed that ethoxylated compounds having a relatively low level of ethoxylation (e.g., additives having an HLB about 4 to 8) were difficult to solubilize in the compositions, but gave excellent foam properties. Ethoxylated compounds having a higher level of ethoxylation (e.g., HLB about 8 to 17) were more easily solubilized, and also exhibited good to excellent foam properties. A mixture of ethoxylate compounds having an HLB about 12 also exhibited excellent foam properties demonstrated by the "+++" bottle foam test result.

| Humectant | Comment | Formula | Stable (S)/ Not Stable (NS) | Bottle Foam Test | Pump Foam Test |
|---|---|---|---|---|---|
| Glycerin | | 1.0TCS/5DPG/15SXS/ 2.5ALS/0.75CAPB/ 5GLY | S | – | + |
| Glycerin | | 0.6TCS/5DPG/15SXS/ 1.5ALS/0.75CAPB/ 10GLY | S | – | – |
| Glycerin | | 0.3TCS/2DPG/15SXS/ 0.75ALS/20GLY | S | – | – |
| Sodium PCA | | 0.3TCS/2DPG/15SXS/ 0.75ALS/1.0PCA | S | – | – |
| Sodium PCA | | 0.3TCS/5DPG/15SXS/ 0.75ALS/0.5PCA | S | + | + |

| Ethoxylated Additive | Comment | Formula | Stable (S)/ Not Stable (NS) | Bottle Foam Test | Pump Foam Test |
|---|---|---|---|---|---|
| Polyoxyethylene (2) stearyl ether (BRIJ 72) | HLB = 4.9 | 0.6TCS/5DPG/15SXS/1.5ALS/ 0.4BRIJ72 | S | +++ | ++ |
| Polyoxyethylene (2) stearyl ether (BRIJ 72) | HLB = 4.9 | 0.6TCS/5DPG/15SXS/1.5ALS/ 0.6BRIJ72 | NS | NT | NT |
| Polyoxyethylene (2) stearyl ether (BRIJ 72) | HLB = 4.9 | 0.6TCS/5DPG/15SXS/1.5ALS/ 0.8BRIJ72 | NS | NT | NT |
| Polyoxyethylene (2) stearyl ether (BRIJ 72) | HLB = 4.9 | 0.6TCS/5DPG/15SXS/1.5ALS/ 1.0BRIJ72 | NS | NT | NT |
| Polyoxyethylene (21) stearyl ether (BRIJ 721) | HLB = 15.5 | 0.6TCS/5DPG/15SXS/1.5ALS/ 1.0BRIJ721 | S | ++ | + |
| BRIJ72/BRIJ721 | Est. HLB = 12.5 | 0.6TCS/5DPG/15SXS/1.5ALS/ 0.75CAPB/0.4BRIJ72/1.0BRIJ721 | S | +++ | ++ |
| ARLASOLVE 200 | HLB = 15.7 | 0.6TCS/5DPG/15SXS/1.5ALS/ 0.75CAPB/1.0ARL200 | S | ++ | ++ |
| PEG7 Glyceryl Cocoate | | 1.0TCS/5DPG/15SXS/2.5ALS/ 0.75CAPB/0.2PEG7GC | S | – | + |
| PEG7 Glyceryl Cocoate | | 0.3TCS/5DPG/15SXS/0.75ALS/ 0.2PEG7GC | S | + | + |
| PEG7 Glyceryl Cocoate | | 0.3TCS/5DPG/15SXS/0.75ALS/ 0.5PEG7GC | S | + | + |
| JEECHEM GL-26 | | 0.3TCS/5DPG/15SXS/0.75ALS/ 0.2JCHMGL26 | S | 0 | 0 |
| ARLACEL 80 | HLB = 4.3 | 0.6TCS/5DPG/15SXS/1.5ALS/ 0.75CAPB/1.0ARL80 | NS | NT | NT |
| ARLACEL 80 | HLB = 4.3 | 0.6TCS/5DPG/15SXS/1.5ALS/ 0.75CAPB/0.5ARL80 | NS | NT | NT |
| ARLACEL 80 | HLB = 4.3 | 0.6TCS/5DPG/15SXS/1.5ALS/ 0.75CAPB/0.3ARL80 | NS | NT | NT |
| ARLACEL 80 | HLB = 4.3 | 0.6TCS/5DPG/15SXS/1.5ALS/ 0.75CAPB/0.1ARL80 | NS | NT | NT |
| LAMESOFT | | 0.3TCS/5DPG/15SXS/0.75ALS/ 0.1LMSFT | S | – | – |

EXAMPLE 5

Phase stability and foam performance attributed to long-chain fatty materials—The compositions of Example 5 show that cetyl alcohol gave outstanding performance in stabilizing foam. In some cases, foam generated in the bottle test lasted several days (vs. under an hour for the control). The amount of cetyl alcohol incorporated into the base formula was 0.05% to 0.5%, by weight. Stearic acid provided improvement in foam properties, and was more difficult to solubilize. The fatty esters generally were more difficult to solubilize in the compositions.

| Long-chain Fatty Material | Comment | Formula | Stable (S)/ Not Stable (NS) | Bottle Foam Test | Pump Foam Test |
|---|---|---|---|---|---|
| Cetyl alcohol | | 0.6TCS/5DPG/15SXS/1.5ALS/0.5CAPB/0.05CETOH | S | + | + |
| Cetyl alcohol | | 0.6TCS/5DPG/15SXS/1.5ALS/0.5CAPB/0.2CETOH | S | ++ | ++ |
| Cetyl alcohol | | 0.6TCS/5DPG/15SXS/1.5ALS/0.5CAPB/0.2CETOH | S | ++ | ++ |
| Cetyl alcohol | | 1.0TCS/5DPG/15SXS/2.5ALS/0.75CAPB/0.5CETOH | S | ++ | ++ |
| Cetyl alcohol | | 0.3TCS/5DPG/0.75ALS/0.1CETOH | S | ++ | ++ |
| Cetyl alcohol | | 1.0TCS/5DPG/15SXS/2.5ALS/0.75CAPB/0.3CETOH | S | +++ | ++ |
| Cetyl alcohol | | 0.6TCS/5DPG/15SXS/1.5ALS/0.5CAPB/0.05CETOH | S | − | + |
| Stearic Acid | | 1.0TCS/5DPG/15SXS/2.5ALS/0.75CAPB/0.15STAC | S | + | + |
| Stearic Acid | | 1.0TCS/5DPG/15SXS/2.5ALS 0.75CAPB/0.2STAC | NS | NT | NT |
| Stearic Acid | | 0.6TCS/5DPG/15SXS/1.5ALS 0.75CAPB/0.2STAC | S | − | + |
| Isopropyl Myristate | | 1.0TCS/5DPG/15SXS/2.5ALS/0.75CAPB/0.2IPM | NS | NT | NT |
| Decyl Oleate | | 0.6TCS/5DPG/15SXS/1.5ALS/0.75CAPB/1.0DCYLOL | NS | NT | NT |
| Decyl Oleate | | 0.6TCS/5DPG/15SXS/1.5ALS/0.75CAPB/0.5DCYLOL | NS | NT | NT |
| Decyl Oleate | | 0.6TCS/5DPG/15SXS/1.5ALS/0.75CAPB/1.0DCYLOL | NS | NT | NT |
| Cetearyl Isononanate | | 0.6TCS/5DPG/15SXS/1.5ALS/0.75CAPB/1.0CETISONON | NS | NT | NT |
| Cetearyl Isononanate | | 0.6TCS/5DPG/15SXS/1.5ALS/0.75CAPB/0.5CETISONON | NS | NT | NT |
| Cetearyl Isononanate | | 0.6TCS/5DPG/15SXS/1.5ALS/0.75CAPB/0.25CETISONON | NS | NT | NT |

EXAMPLE 6

Phase stability and foam performance attributed to other additives—ISML (isostearylmorpholine lactate) was a useful additive in these tests. Petrolatum was difficult to solubilize in the base formulae of the invention. Petrolatum also is a component of at least two recently introduced commercial antimicrobial hand wash products (see Table 2 below). Commercial product E also contains dimethicone.

| Other Additives | Comment | Formula | Stable (S)/ Not Stable (NS) | Bottle Foam Test | Pump Foam Test |
|---|---|---|---|---|---|
| MACKERNIUM 1216 | | 0.3TCS/5DPG/15SXS/0.75ALS/0.1MAC1216 | S | − | + |
| MACKERNIUM SFES | | 0.3TCS/5DPG/15SXS/0.75ALS/0.5SFES | S | − | + |
| OLIVEM 400 | | 0.3TCS/5DPG/15SXS/0.75ALS/0.5OL400 | S | − | + |
| PROMIDIUM CC | | 0.6TCS/5DPG/15SXS/1.5ALS/1PCC | S | − | 0 |
| PROMIDIUM CO | | 0.6TCS/5DPG/15SXS/1.5ALS/0.75CAPB/0.4PCO | S | NT | NT |
| Mineral Oil | | 0.6TCS/5DPG/15SXS/1.5ALS/0.75CAPB/0.5MO | NS | NT | NT |
| Mineral Oil | | 0.6TCS/5DPG/15SXS/1.5ALS/0.75CAPB/0.25MO | NS | NT | NT |
| Mineral Oil | | 0.6TCS/5DPG/15SXS/1.5ALS/0.75CAPB/0.13MO | NS | NT | NT |
| Mineral Oil | | 0.6TCS/5DPG/15SXS/1.5ALS/0.75CAPB/0.05MO | NS | NT | NT |

-continued

| Other Additives | Comment | Formula | Stable (S)/ Not Stable (NS) | Bottle Foam Test | Pump Foam Test |
|---|---|---|---|---|---|
| Mineral Oil | | 0.6TCS/5DPG/15SXS/1.5ALS/0.75CAPB/ 0.025MO | NS | NT | NT |
| Petrolatum | | 0.6TCS/5DPG/15SXS/1.5ALS/0.5CAPB/ 0.05PETR | NS | NT | NT |
| Petrolatum | | 0.6TCS/5DPG/15SXS/1.5ALS/0.5CAPB/0.1PETR | NS | NT | NT |
| ISML | | 0.3TCS/5DPG/15SXS/0.75ALS/0.1ISML | S | + | + |
| ISML | | 1.0TCS/5DPG/15SXS/2.5ALS/0.75CAPB/ 0.21ISML | S | − | + |
| Sr (OAc)$_2$ | | 1.0TCS/5DPG/15SX5/2.5ALS/0.75CAPB/ 0.2Sr (OAc)$_2$ | NS | NT | NT |
| Sr (OAc)$_2$ | | 1.0TCS/5DPG/15SXS/2.5ALS/0.75CAPB/ 0.2Sr (OAc)$_2$ | NS | NT | NT |

TABLE 2

Ingredients Statements for Commerical Antimicrobial Hand Washer

| Commercial Product E (ingredients statement on label)) | Commercial Product F (ingredients statement on labels) |
|---|---|
| ACTIVE INGREDIENT: Triclosan | ACTIVE INGREDIENT: 0.25% TRICLOSAN |
| OTHER INGREDIENTS: | INACTIVE INGREDIENTS: |
| WATER | WATER |
| SODIUM LAURETH SULFATE | PETROLATUM |
| COCAMIDOPROPYL BETAINE | SODIUM LAUROYL SARCOSINATE |
| PETROLATUM | SODIUM LAUROAMPHOACETATE |
| DIMETHICONE | AMMONIUM LAURYL SULFATE |
| LAURIC ACID | AMMONIUM LAURETH SULFATE |
| DECYL GLUCOSIDE | LAURIC ACID |
| ACRYLATES/C10–30 ALKYL ACRYLATE CROSSPOLYMER | TRIHYDROXYSTEARIN |
| HYDROXYPROPYL METHYLCELLULOSE | GUAR HYDROXYPROPYLTRIMONIUM CHLORIDE |
| TRIETHANOLAMINE | CITRIC ACID |
| FRAGRANCE | SODIUM BENZOATE |
| DMDM HYDANTOIN | DISODIUM EDTA |
| POLYQUATERNIUM-39 | FRAGRANCE |
| POLYQUATERNIUM-7 | GLYCERIN |
| TETRASODIUM EDTA | PEG-90 STEARATE |
| D&C ORANGE NO. 4 | METHYLCHLOROISOTHIAZOLINONE |
| FD&C RED NO. 40 | |

EXAMPLE 7

Phase stability and foam performance attributed to combinations of additives—Several tested compositions, especially those containing a combination of cetyl (or cetearyl) alcohol, stearic acid, and/or glycerin, exhibited excellent foam stability.

| Combinations | Formula | Stable (S)/ Not Stable (NS) | Bottle Foam Test | Pump Foam Test |
|---|---|---|---|---|
| Glycerin/Cetyl Alcohol | 0.6TCS/5DPG/15SXS/1.5ALS/0.5CAPB/ 5GLY/0.2CETOH | S | +++ | ++ |
| Glycerin/Cetyl Alcohol | 0.6TCS/5DPG/15SXS/1.5ALS/0.5CAPB/ 10GLY/0.2CETOH | S | +++ | ++ |
| Glycerin/Cetyl Alcohol | 0.6TCS/5DPG/15SXS/1.5ALS/0.75CAPB/ 10GLY/0.2CETOH | S | +++ | ++ |
| Glycerin/Cetyl Alcohol | 0.6TCS/5DPG/15SXS/1.5ALS/0.75CAPB/ 10GLY/0.2CETOH | S | +++ | ++ |
| Glycerin/Cetyl Alcohol | 0.6TCS/5DPG/15SXS/1.5ALS/0.75CAPB/ 10GLY/0.3CETOH | NS | NT | NT |
| Glycerin/Cetyl Alcohol | 0.6TCS/5DPG/15SXS/1.5ALS/0.75CAPB/ 10GLY/1.0CETOH | NS | NT | NT |
| Glycerin/Cetyl Alcohol | 0.6TCS/5DPG/15SXS/1.5ALS/0.75CAPB/ 10GLY/0.4CETOH | NS | NT | NT |

-continued

| Combinations | Formula | Stable (S)/ Not Stable (NS) | Bottle Foam Test | Pump Foam Test |
|---|---|---|---|---|
| Glycerin/Cetyl Alcohol | 0.6TCS/5DPG/15SXS/1.5ALS/0.75CAPB/ 10GLY/0.2CETOH | S | +++ | ++ |
| Glycerin/Stearic Acid | 0.6TCS/5DPG/15SXS/1.5ALS/0.75CAPB/ 10GLY/0.15STAC | NS | NT | NT |
| Glycerin/Stearic Acid/Cetyl Alcohol | 0.6TCS/5DPG/15SXS/1.5ALS/0.75CAPB/ 10GLY/0.05STAC/0.15CETOH | S | +++ | ++ |
| Glycerin/Stearic Acid/Cetyl Alcohol | 0.6TCS/5DPG/15SXS/1.13ALS/0.37CAPB/ 5GLY/0.05STAC/0.15CETOH | S | +++ | ++ |
| Glycerin/Stearic Acid/Cetyl Alcohol | 0.6TCS/5DPG/15SXS/1.5ALS/0.5CAPB/ 10GLY/0.025STAC/0.15CETOH | S | +++ | ++ |
| Glycerin/Stearic Acid/Cetyl Alcohol | 0.6TCS/5DPG/15SXS/1.13ALS/0.37CAPB/ 10GLY/0.05STAC/0.15CETOH | NS | NT | NT |
| Glycerin/Stearic Acid/Cetyl Alcohol | 0.6TCS/5DPG/15SXS/1.5ALS/0.75CAPB/ 10GLY/0.05STAC/0.2CETOH | NS | NT | NT |
| Glycerin/Stearic Acid/Cetyl Alcohol | 0.6TCS/5DPG/15SXS/1.13ALS/0.37CAPB/ 7.5GLY/0.2CETOH/0.05STAC | NS | NT | NT |
| Glycerin/Stearic Acid/Cetyl Alcohol | 0.6TCS/5DPG/15SXS/1.5ALS/0.5CAPB/ 10GLY/0.02CETOH/0.05STAC | NS | NT | NT |
| Glycerin/Stearic Acid/Cetyl Alcohol | 0.6TCS/5DPG/15SXS/1.0ALS/0.5CAPB/ 10GLY/0.15CETOH/0.05STAC | NS | NT | NT |
| Glycerin/Stearic Acid/Cetyl Alcohol | 0.6TCS/5DPG/15SXS/1.5ALS/0.75CAPB/ 10GLY/0.1STAC/0.2CETOH | NS | NT | NT |
| Glycerin/Stearic Acid/Cetyl Alcohol | 0.6TCS/5DPG/15SXS/1.5ALS/0.5CAPB/ 10GLY/0.2CETOH/0.05STAC | NS | NT | NT |
| Glycerin/Stearic Acid/Cetyl Alcohol | 0.6TCS/5DPG/15SXS/1.5ALS/0.5CAPB/ 5GLY/0.2CETOH/0.05STAC | NS | NT | NT |
| SLES2/Glycerin/Stearic Acid/Cetyl Alcohol | 0.6TCS/5DPG/15SXS/1.13SLES2/0.37CAPB/ 10GLY/0.05STAC/0.15CETOH | S | +++ | ++ |
| SLES2/Glycerin/Stearic Acid/Cetyl Alcohol | 0.6TCS/5DPG/15SXS/1.5SLES2/0.5CAPB/ 10GLY/0.05STAC/0.15CETOH | S | +++ | ++ |
| SLES2/Glycerin/Stearic Acid/Cetyl Alcohol | 0.6TCS/5DPG/15SXS/1.13SLES2/0.37CAPB/ 7.5GLY/0.05STAC/0.2CETOH | NS | NT | NT |
| Cetyl Alcohol/PROMIDIUM CC | 0.6TCS/5DPG/15SXS/1.5ALS/0.75CAPB/ 0.3CETOH/0.5PCC | S | ++ | ++ |
| Cetyl Alcohol/PROMIDIUM CC | 0.6TCS/5DPG/15SXS/0.5CETOH/1.5PCC | NS | NT | NT |
| Stearic Acid/Cetyl Alcohol | 0.6TCS/5DPG/15SXS/1.5ALS/0.75CAPB/ 0.15CETOH/0.025STAC | S | +++ | ++ |
| Stearic Acid/Cetyl Alcohol | 0.6TCS/5DPG/15SXS/1.5ALS/0.5CAPB/ 0.15CETOH/0.05STAC | S | +++ | ++ |
| Sodium PCA/Glycerin | 0.6TCS/5DPG/15SXS/1.5ALS/0.75CAPB/ 10GLY/.5PCA | S | – | – |
| JAGHP60/MACKALINE SFES | 0.3TCS/5DPG/15SXS/0.75ALS/ 0.05JAGHP60/0.5SFES | S | + | + |
| Sodium PCA/JAGHP60 | 0.3TCS/5DPG/15SXS/0.75ALS/ 0.05JAGHP60/1.0PCA | S | 0 | – |
| JAGHP60/OLIVEM 400 | 0.3TCS/5DPG/15SXS/0.75ALS/ 0.05JAGHP60/0.5OLIVM400 | S | – | + |
| Lauricidin/MACKALINE SPES | 0.3TCS/5DPG/15SXS/0.75ALS/0.5SFES/ 0.5LRCDN | NS | NT | NT |
| Polyquat10/Cetyl Alcohol/Glycerin/NaPCA | 0.4TCS/5DPG/15SXS/0.75ALS/0.25PQ10/ 0.1CETOH/3GLY/1.5NaPCA | S | +++ | ++ |
| LAMESOFT/Glycerin/NaPCA/ JAGHP60 | 0.4TCS/5DPG/15SXS/0.75ALS/0.5LAMSFT/ 2.5GLY/1.5NaPCA/0.04JAGHP60/0.1CETOH | S | +++ | ++ |
| NATROSOL HEC/PEG-75 Lanolin/PPG-5-Ceteth20 | 0.3TCS/5DPG/15SXS/0.75ALS/ 0.05NTSLHEC/0.5PEG-75LAN/0.5PPG5CET20 | S | ++ | + |
| NATROSOL HEC/Sunflower oil | 0.3TCS/5DPG/15SXS/0.75ALS/ 0.05NTSLHEC/1.0SUNFLWR | S | – | 0 |
| NATROSOL HEC/GlycerinPOE | 0.3TCS/5DPG/15SXS/0.75ALS/ 0.05NTSLHEC/0.5GLYPOE | S | – | – |
| NATROSOL HEC/NaPCA | 0.3TCS/5DPG/15SXS/0.75ALS/ 0.05NTSLHEC/1.0NaPCA | S | – | – |
| JAGHP60/Sunflower oil | 0.3TCS/5DPG/15SXS/0.75ALS/ 0.04JAGHP60/1.0SUNFLWR | S | – | + |
| JAGHP60/Sunflower oil/VitE | 0.3TCS/5DPG/15SXS/0.75ALS/ 0.03JAGHP60/1.0SUNFLWR/0.01VitE | S | – | + |
| JAGHP60/NaPCA | 0.3TCS/5DPG/15SXS/0.75ALS/ 0.05JAGHP60/0.5NaPCA | S | + | + |
| NaPCA/MACKPRO WLW/JAGHP60/ Aloe Vera | 0.3TCS/5DPG/15SXS/0.75ALS/ 0.04JAGHP60/1.0NaPCA/0.5WLW/0.01AV | S | + | – |
| NaPCA/ISML/JAGHP60/Aloe Vera | 0.3TCS/5DPG/15SXS/0.75ALS/ 0.04JAGHP60/1.0NaPCA/0.5ISML/0.01AV | S | ++ | + |
| NaPCA/MACKALENE 1216/ JAGHP60/VitaminEOAc | 0.3TCS/5DPG/15SXS/0.75ALS/ 0.04JAGHP60/1.0NaPCA/0.5M1216/0.01VitE | S | + | + |
| NaPCA/Glycerin/Cetyl Alcohol | 0.4TCS/5DPG/15SXS/0.75ALS/0.75CAPB/ 1.5NaPCA/3.8GLY/0.1CETOH/0.1ALOE | S | +++ | ++ |

-continued

| Combinations | Formula | Stable (S)/ Not Stable (NS) | Bottle Foam Test | Pump Foam Test |
|---|---|---|---|---|
| NaPCA/Polyquat10/Cetyl Alcohol/LAMESOFT | 0.4TCS/5DPG/15SXS/0.75ALS/0.5NaPCA/ 0.25CQSC240C/0.1CETOH/0.5LMSFT | S | +++ | NT |
| NaPCA/Polyquat10/Cetyl Alcohol/VARISOFT | 0.4TCS/5DPG/15SXS/0.75ALS/0.5NaPCA/ 0.25CQSC240C/0.1CETOH/0.5VRSFT | S | +++ | NT |
| NaPCA/Polyquat10/Cetyl Alcohol/Glycerin/LAMESOFT | 0.3TCS/5DPG/15SXS/0.75ALS/0.5LMSFT/ 0.5NaPCA/3GLY/0.1CETOH/0.25CQSC240C | S | ++ | ++ |
| NaPCA/Polyquat10/Cetyl Alcohol/Glycerin | 0.3TCS/5DPG/15SXS/0.75ALS/1.0NaPCA/ 3GLY/0.1CETOH/0.25CQSC240C | S | ++ | ++ |

EXAMPLE 8

Antimicrobial Performance in Time Kill Tests. Results for antimicrobial efficacy are summarized in the following table—Unless otherwise indicated, the values are for log reduction of Serratia marcescens at 30 seconds. Values for "Sa," "Ec," and "Kp" refer to *Staphylococcus aureus*, *Escherichia coli* and *Klebsiella pneumoniae*, respectively, at 30 seconds. The log reduction value for the test composition appears first, followed by the log reduction value for an appropriate control sample (in the table below, "//(cna)" means control not available). A log reduction value within about 1 log of the control sample is considered highly efficacious. Values for *Serratia marcescens* vary somewhat, between about log 2 to >log 4 reduction, for control samples.

| Description | Formula | Time Kill Results |
|---|---|---|
| Control Formula 1 | 1.0TCS/5DPG/15SXS/2.5ALS/0.75CAPB | >4.14(Sa30)/>4.60(Ec30) |
| Control Formula 2 | 0.6TCS/5DPG/15SXS/1.5ALS/0.75CAPB | 4.73/— |
| Control Formula 3 | 0.6TCS/5DPG/15SXS/1.5ALS/0.5CAPB | 2.74/— |
| Control Formula 4a | 0.3TCS/5DPG/15SXS/0.75ALS | >4.91/— |
| Control Formula 4b | 0.3TCS/5DPG/15SXS/0.75ALS | >4.86/— |
| Control Formula 4c | 0.3TCS/5DPG/15SXS/0.75ALS | 3.15/— |
| Control Formula 4d | 0.3TCS/5DPG/15SXS/0.75ALS | >4.83/— |
| Control Formula 4e | 0.3TCS/5DPG/15SXS/0.75ALS | 3.17/— |
| Control Formula 4f | 0.3TCS/5DPG/15SXS/0.75ALS | >4.90(Sa)/— >5.00(Ec)/— 4.47(Kp)/— 2.97(Sm)/— |
| Control Formula 4g | 0.6TCS/5DPG/15SXS/1.5ALS/1PCC | 4.28 |
| Sodium PCA/JAGHP60 (used as an "approximate" control) (Control 5) | 0.3TCS/5DPG/15SXS/0.75ALS/0.05JAGHP60/ 1.0PCA | 2.99/— |
| Primary Surfactants | | |
| Sodium Lauryl Ether Sulfate (2-mole) | 1.0TCS/5DPG/15SXS/2.5SLES2/0.75CAPB | >4.69(Sa30)/4.54(Ec30)// (cna) |
| Ammonium Cocyl Isethionate | 1.0TCS/5DPG/15SXS/2.5ACI/0.75CAPB | >4.69(Sa30)/4.29(Ec30)// (cna) |
| Polymers | | |
| PVP K30 | 1.0TCS/5DPG/15SXS/2.5ALS/0.75CAPB/ 0.1PVPK30 | >4.14(Sa)/>4.60(Ec)//>4.14/ >4.60(1) |
| JAGUAR HP-60 | 0.3TCS/5DPG/15SXS/0.75ALS/0.1HP60 | >4.86/>4.86(4b) |
| CELQUAT SC-230M | 0.3TCS/5DPG/15SXS/0.75ALS/0.1CQSC230M | >4.86/>4.86(4b) |
| CELQUAT SC-230M | 0.6TCS/5DPG/15SXS/1.5ALS/0.75CAPB/ 0.5CQSC230M | 4.38/4.73(2) |
| CELQUAT H-100 | 0.6TCS/5DPG/15SXS/1.5ALS/0.75CAPB/ 0.5CQH100 | 4.38/4.73(2) |
| NATROSOL 250 HHR | 0.3TCS/5DPG/15SXS/0.75ALS/0.05NATSOL250HHR | >4.86/>4.86(4b |
| CARBOWAX 540 | 0.6TCS/5DPG/15SXS/1.5ALS/0.5CAPB/ 1.0CWAX540 | 4.73/>4.73(4d) |
| CARBOWAX 900 | 0.6TCS/5DPG/15SXS/1.5ALS/0.5CAPB/ 1.0CWAX900 | 4.63/>4.73(4d) |
| FLEXAN 130 | 0.6TCS/5DPG/15SXS/1.5ALS/0.5CAPB/ 1.0FLEX130 | 4.63/>4.73(4d) |
| Protein Derivatives | | |
| MACKPRO WWP | 0.3TCS/5DPG/15SXS/0.75ALS/1.0WWP | 3.41/>4.91(4a) |
| MACKPRO WWP | 0.3TCS/5DPG/15SXS/0.75ALS/0.5WWP | 3.95/>4.91(4a) |
| MACKPRO NLW | 0.3TCS/5DPG/15SXS/0.75ALS/0.2NLW | >4.86/>4.86(4b) |
| Silicone Derivatives | | |
| Dimethicone Propyl PG Betaine | 0.3TCS/5DPG/15SXS/0.75ALS/0.2DIMETHPGB | >4.86/>4.86(4b) |

-continued

| Description | Formula | Time Kill Results |
|---|---|---|
| Stearyl Methicone | 0.3TCS/5DPG/15SXS/0.75ALS/0.05STMETH | 3.60/>4.91(4a) |
| Dow Corning 193 | 0.3TCS/5DPG/15SXS/0.75ALS/0.2DC193 | 4.41/>4.86(4b) |
| Humectants | | |
| Glycerin | 1.0TCS/5DPG/15SXS/2.5ALS/0.75CAPB/5GLY | >4.14(Sa)/>4.60(Ec)//>4.14/>4.60(1) |
| Sodium PCA | 0.3TCS/2DPG/15SXS/0.75ALS/0.5PCA | >4.86/>4.86(4b) |
| Ethoxylated Derivative | | |
| Polyoxyethylene (2) stearyl ether (BRIJ 72) | 0.6TCS/5DPG/15SXS/1.5ALS/0.4BRIJ72 | 2.31/4.28(4g) |
| Polyoxyethylene (21) stearyl ether (BRIJ 721) | 0.6TCS/5DPG/15SXS/1.5ALS/1.0BRIJ721 | 2.33/4.28(4g) |
| ARLASOLVE 200 | 0.6TCS/5DPG/15SXS/1.5ALS/0.75CAPB/1.0ARL200 | |
| PEG7 Glyceryl Cocoate | 0.3TCS/5DPG/15SXS/0.75ALS/0.5PEG7GC | >4.86/>4.86(4b) |
| LAMESOFT | 0.3TCS/5DPG/15SXS/0.75ALS/0.1LMSFT | 3.73/>4.91(4a) |
| Long-chain Fatty Materials | | |
| Cetyl alcohol | 0.6TCS/5DPG/15SXS/1.5ALS/0.5CAPB/0.05CETOH | 2.56/2.74(3) |
| Cetyl alcohol | 0.6TCS/5DPG/15SXS/1.5ALS/0.5CAPB/0.2CETOH | 2.70/2.74(3) |
| Cetyl alcohol | 0.6TCS/5DPG/15SXS/1.5ALS/0.5CAPB/0.1CETOH | 2.65/2.74(3) |
| Stearic Acid | 1.0TCS/5DPG/15SXS/2.5ALS/0.75CAPB/0.2StAc | >4.14(Sa)/>4.60(Ec)//>4.14/>4.60(3) |
| Lipid-like Materials | | |
| Canola Oil | 0.6TCS/5DPG/25SXS/1.5ALS/0.75CAPB/10GLY/0.1CANOL | 2.96/3.15(4c) |
| Other Emollients | | |
| MACKERNIUM 1216 | 0.3TCS/5DPG/15SXS/0.75ALS/0.1MAC1216 | >4.86/>4.86(4b) |
| PROMIDIUM CC | 0.6TCS/5DPG/15SXS/1.5ALS/1PCC | 4.28/4.28(4g) |
| ISML | 0.3TCS/5DPG/15SXS/0.75ALS/0.1ISML | 4.76/>4.86(4b) |
| ISML | 1.0TCS/5DPG/15SXS/2.5ALS/0.75CAPB/0.21ISML | >4.69(Sa30)/4.06(Ec)//(cna) |
| $Sr(OAc)_2$ | 1.0TCS/5DPG/15SXS/2.5ALS/0.75CAPB/0.2Sr(OAc)$_2$ | >4.69(Sa30)/3.24(Ec30)//(cna) |
| JEECHEM GL-26 | 0.3TCS/5DPG/15SXS/0.75ALS/0.2JCHMGL26 | >4.86/>4.86(4b) |
| Combinations | | |
| Glycerin/Cetyl Alcohol | 0.6TCS/5DPG/15SXS/1.5ALS/0.5CAPB/5GLY/0.2CETOH | 2.77/2.74(3) |
| Glycerin/Cetyl Alcohol | 0.6TCS/5DPG/15SXS/1.5ALS/0.5CAPB/10GLY/0.2CETOH | 3.00/2.74(3) |
| Glycerin/Cetyl Alcohol | 0.6TCS/5DPG/15SXS/1.5ALS/0.75CAPB/10GLY/0.2CETOH | 2.38/3.15(4c) |
| Glycerin/Stearic Acid/Cetyl Alcohol | 0.6TCS/5DPG/15SXS/1.5ALS/0.75CAPB/10GLY/0.05STAC/0.15CETOH | 2.46/3.15(4c) |
| Glycerin/Stearic Acid/Cetyl Alcohol | 0.6TCS/5DPG/15SXS/1.13ALS/0.37CAPB/5GLY/0.05STAC/0.15CETOH | 2.41/3.15(4c) |
| Glycerin/Stearic Acid/Cetyl Alcohol | 0.6TCS/5DPG/15SXS/1.13ALS/0.37CAPB/10GLY/0.05STAC/0.15CETOH | 2.70/3.15(4c) |
| SLES2/Glycerin/Stearic Acid/Cetyl Alcohol | 0.6TCS/5DPG/15SXS/1.13SLES2/0.37CAPB/10GLY/0.05STAC/0.15CETOH | 2.30/3.15(4c) |
| SLES2/Glycerin/Stearic Acid/Cetyl Alcohol | 0.6TCS/5DPG/15SXS/1.5SLES2/0.5CAPB/10GLY/0.05STAC/0.15CETOH | 2.31/3.15(4c) |
| Stearic Acid/Cetyl Alcohol | 0.6TCS/5DPG/15SXS/1.5ALS/0.5CAPB/0.15CETOH/0.05STAC | 2.59/3.15(4c) |
| JAGHP60/MACKALINE SFES | 0.3TCS/5DPG/15SXS/0.75ALS/0.05JAGHP60/0.5SFES | 1.22/2.99(5) |
| JAGHP60/OLIVEM 400 | 0.3TCS/5DPG/15SXS/0.75ALS/0.05JAGHP60/0.5OLIVM400 | 1.37/2.99(5) |
| Sodium PCA/JAGHP60 | 0.3TCS/5DPG/15SXS/0.75ALS/0.05JAGHP60/1.0PCA | 2.99/2.99(5) |
| Polyquat10/Cetyl Alcohol/Glycerin/NaPCA/Aloe Vera | 0.4TCS/5DPG/15SXS/0.75ALS/0.75CAPB/0.25CQSC240C/0.1CETOH/3GLY/1.5NaPCA/0.1ALOE | 4.30/>4.83(4d) |
| LAMESOFT/Glycerin/NaPCA/JAGHP60/Aloe Vera | 0.4TCS/5DPG/15SXS/0.75ALS/0.75CAPB/0.5LAMSFT/2.5GLY/1.5NaPCA/0.04JAGHP60/0.1ALOE | 4.53/>4.83(4d) |
| NATROSOL HEC/PEG-75 Lanolin/PPG-5-Ceteth20 | 0.3TCS/5DPG/15SXS/0.75ALS/0.05NTSLHEC/0.5PEG-75LAN/0.5PPG5CET20 | 0.79/2.99(5) |
| NATROSOL HEC/Sunflower oil | 0.3TCS/5DPG/15SXS/0.75ALS/0.05NTSLHEC/1.0SUNFLWR | 1.22/2.99(5) |
| NATROSOL HEC/GlycerinPOE | 0.3TCS/5DPG/15SXS/0.75ALS/0.05NTSLHEC/0.5GLYPOE | 1.53/2.99(5) |

| Description | Formula | Time Kill Results |
|---|---|---|
| NATROSOL HEC/NaPCA | 0.3TCS/5DPG/15SXS/0.75ALS/0.05NTSLHEC/<br>1.0NaPCA | 2.16/2.99(5) |
| JAGHP60/Sunflower oil | 0.3TCS/5DPG/15SXS/0.75ALS/0.04JAGHP60/<br>1.0SUNFLWR | 1.43/2.99(5) |
| JAGHP60/SunflowerOil/VitE | 0.3TCS/5DPG/15SXS/0.75ALS/0.03JAGHP60/<br>1.0SUNFLWR/0.01VitE | 2.16/2.99(5) |
| JAGHP60/NaPCA | 0.3TCS/5DPG/15SXS/0.75ALS/0.05JAGHP60/<br>0.5NaPCA | 3.95/>4.91(4a) |
| NaPCA/MACKPROWLW/JAGHP60/<br>Aloe Vera | 0.3TCS/5DPG/15SXS/0.75ALS/0.04JAGHP60/<br>1.0NaPCA/0.5WLW/0.01AV | 3.14/3.17(4e) |
| NaPCA/ISML/JAGHP60/Aloe<br>Vera | 0.3TCS/5DPG/15SXS/0.75ALS/0.04JAGHP60/<br>1.0NaPCA/0.5ISML/0.01AV | 3.00/3.17(4e) |
| NaPCA/Mackalene1216/<br>JAGHP60/VitaminEOAc | 0.3TCS/5DPG/15SXS/0.75ALS/0.04JAGHP60/<br>1.0NaPCA/0.5M1216/0.01VitE | 1.88/3.17(4e) |
| NaPCA/Glycerin/Cetyl<br>Alcohol/Aloe Vera | 0.4TCS/5DPG/15SXS/0.75ALS/0.75CAPB/<br>1.5NaPCA/3.8GLY/0.1CETOH/0.1ALOE | 4.58/>4.83(4d) |
| NaPCA/Polyquat10/Cetyl<br>Alcohol/LAMESOFT/Aloe<br>Vera | 0.4TCS/5DPG/15SXS/0.75ALS/0.75CAPB/<br>0.5NaPCA/0.25CQSC240C//0.1CETOH/0.5LMSFT/<br>0.1ALOE | >4.73/>4.73(4d) |
| NaPCA/Polyquat10/Cetyl<br>Alcohol/VARISOFT/Aloe<br>Vera | 0.4TCS/5DPG/15SXS/0.75ALS/0.75CAPB/<br>0.5NaPCA/0.25CQS240C//0.1CETOH/0.5VRSFT<br>0.1ALOE | 4.25/>4.73(4d) |
| NaPCA/Polyquat10/Cetyl<br>Alcohol/Glycerin/Aloe<br>Vera | 0.4TCS/5DPG/15SXS/0.75ALS/0.75CAPB/<br>1.0NaPCA/3GLY/0.1CETOH/0.25CQSC240C/<br>0.1ALOE | >4.90(Sa)/>4.90(4f)<br>>5.00(Ec)/>5.00(4f)<br>4.65(Kp)/4.47(4f)<br>2.94(Sm)/2.97(4f) |
| NaPCA/Polyquat10/Cetearyl<br>Alcohol/Glycerin/Aloe<br>Vera | 0.4TCS/5DPG/15SXS/0.75ALS/0.75CAPB/<br>0.5LMSFT/0.5NaPCA/3GLY/0.1CETOH/<br>0.25CQSC240C/0.1ALOE | >4.90(Sa)/>4.90(4f)<br>>5.00(Ec)/>5.00(4f)<br>4.70(Kp)/4.47(4f)<br>2.85(Sm)/2.97(4f) |

EXAMPLE 9

Antimicrobial Performance Tests (Broad Spectrum Efficacy)—The following embodiment of the present invention was tested:

COMPOSITION A (by weight): 0.46 TCS/5DPG/15SXS/ 0.75CAPB/0.129 Disodium Phosphate/0.066 Citric Acid, buffer (pH≅6)/0.1 Cetyl Alcohol/0.05 fragrance/1 Sodium PCA/2.97GLY/0.25 Polyquaternium-100/0.1 Aloe Vera Gel/0.15 Methyl Paraben/0.05 Propylparaben/0.00005 FD&C Red #4/0.000025 Yellow #5.

Time kill tests were performed to compare Composition A of the present invention to several commercially available Health Care Personnel Hand Wash products (i.e., HCPHW-E, F, G, H. I, J) and to several commercially available retail antibacterial hand wash products. Three nonmedicated retail liquid hand soaps also were tested for comparison. The tests evaluated efficacy against a broad spectrum of twenty-four different microorganisms. Test organisms were selected to represent both transient and resident organisms, Gram negative bacteria (such as *Pseudomonas aeruginosa, Escherichia coli, Klebsiella pneumoniae, Salmonella typhimurium*), and Gram positive bacteria (such as *Staphylococcus aureus, Staphylococcus epidermidis*, and *Streptococcus pyogenes*). The compositions were tested with sampling taking place at 30 seconds and 1 minute.

The test organisms represented a broad spectrum of both Gram positive and Gram negative organisms commonly associated with nosocomial infections. For the health care products, five additional test organisms were added as a result of a health care survey, including several antibiotic resistant strains of bacteria. The following Time Kill Summary charts summarize bacterial kill results for Composition A vs. several Health care Personnel Hand wash Products.

The Time Kill Summary charts summarize data for both Health care Personnel Hand washes and retail liquid hand soaps, and includes a number of organisms of the total tested that were reduced by greater than 3, 2, or 1 log within 30 seconds. Antimicrobial potential can be classified based on a product's ability to reduce the number of organisms in logarithms. A product that is unable to achieve a 1 log reduction shows minimal activity against that specific organism. A one log reduction is considered moderate activity, whereas a greater than 2 or 3 log reduction is considered strong antibacterial activity in vitro.

The summarized results demonstrate a significantly superior efficacy for Composition A versus the twenty-four test organisms (30 second time-kill). Composition A performed significantly better than each of the commercially available Health Care Personnel Hand Wash products tested (i.e., HCPHW-E through J) at reducing the number and type of microorganisms encountered in health care settings. Further, compared to the leading liquid hand soaps and health care products, Composition A was superior at reducing more types of test organisms by greater than 3 logs within 30 seconds. Composition A reduced 19 of 24 organisms tested by greater than 3 log units within 30 seconds. The closest comparative composition, HCPHW-I, reduced 16 of 24 organisms greater than 3 log units. The remaining comparative compositions showed moderate to minimal antimicrobial activity.

Time Kill Summary-I
Log Reduction

| Test Organisms | Composition A 30 Sec. | Composition A 1 Min. | Commercial Product HCPHW-E 30 Sec. | Commercial Product HCPHW-E 1 Min. | Commercial Product HCPHW-F 30 Sec. | Commercial Product HCPHW-F 1 Min. | Commercial Product HCPHW-G 30 Sec. | Commercial Product HCPHW-G 1 Min. | Commercial Product HCPHW-H 30 Sec. | Commercial Product HCPHW-H 1 Min. | Commercial Product HCPHW-I 30 Sec. | Commercial Product HCPHW-I 1 Min. |
|---|---|---|---|---|---|---|---|---|---|---|---|---|
| *Staphylococcus aureus* (ATCC 6538) | 5.07 | >5.17 | 1.31 | 2.14 | 1.05 | 1.43 | 2.98 | 4.38 | 1.75 | 2.55 | 2.94 | 4.23 |
| *Staphylococcus epidermis* (ATCC 12228) | 3.35 | 4.41 | 0.46 | 0.47 | 0.23 | 0.42 | 0.38 | 0.65 | 0.78 | 1.00 | 5.02 | 4.66 |
| *Stphylococcus aureus* MRSA (ATCC 33592) | 0.98 | 1.93 | 0.05 | 0.17 | 0.10 | 0.12 | 0.31 | 0.50 | 0.19 | 0.23 | 1.73 | 2.80 |
| *Streptococcus pneumoniae* (ATCC 6303) | >3.07 | >3.07 | >3.07 | >3.07 | >3.07 | >3.07 | >3.07 | >3.07 | >3.07 | >3.07 | 1.91 | 1.55 |
| *Streptococcus pyogenes* (ATCC 19615) | >4.11 | >4.11 | 4.01 | >4.11 | 3.80 | >4.11 | >3.98 | >3.98 | >4.11 | >4.11 | >3.97 | >3.97 |
| *Pseudomonas aeruginosa* (clinical isolate) | >5.23 | >5.23 | >5.23 | >5.23 | >5.23 | >5.23 | >5.23 | >5.23 | >5.23 | >5.23 | >5.23 | >5.23 |
| *Pseudomonas aeruginosa* (ATCC 9027) | >5.25 | >5.25 | >5.25 | >5.25 | >5.25 | >5.25 | >5.25 | >5.25 | >5.25 | >5.25 | >4.21 | >4.21 |
| *Klebsiella pneumoniae* (ATCC 11296) | >5.07 | >5.07 | 2.26 | 2.76 | 4.52 | >5.07 | 5.02 | >5.07 | 3.45 | 4.18 | >4.27 | >4.27 |
| *Burkholderia cepacia* (ATCC 25416) | >4.92 | >4.92 | 0.00 | 0.05 | 1.56 | 4.59 | 2.08 | 4.92 | 0.05 | 0.47 | 2.42 | 1.65 |
| *Serratia marcescens* (ATCC 14756) | 3.96 | >5.47 | 0.16 | 0.27 | 0.02 | 0.07 | 0.15 | 0.51 | 0.18 | 0.23 | >4.59 | >4.59 |
| *Shigella sonnei* (ATCC 11060) | 4.22 | >5.23 | 3.75 | 5.03 | 0.63 | 1.63 | 2.33 | 5.23 | 3.65 | >5.23 | 4.18 | >4.36 |
| *Salmonella choleraseuis* (ATCC 13076) | >5.27 | >5.27 | 1.83 | 3.66 | 0.67 | 1.32 | 5.07 | >5.27 | 1.31 | 2.91 | >5.64 | >5.64 |
| *Salmonella choleraseuis* (typhi) (ATCC 6539) | >5.20 | >5.20 | 2.02 | >5.20 | 0.93 | 3.56 | 5.04 | >5.20 | 3.14 | >5.20 | >4.59 | >4.59 |
| *Stenotrophomonas maltophilia* (ATCC 13637) | >5.11 | >5.11 | 4.95 | 4.89 | >5.11 | 4.95 | >5.11 | >5.11 | >5.11 | >5.11 | >4.97 | >4.97 |
| *Enterobacter aerogenes* (ATCC 13048) | 2.61 | >5.23 | 0.43 | 0.63 | 0.30 | 0.45 | 0.56 | 1.46 | 0.60 | 0.73 | 2.60 | 3.78 |
| *Escherichia coli* (ATCC 11229) | >5.14 | >5.14 | 0.72 | 1.06 | 0.66 | 0.96 | 1.10 | 1.89 | 2.08 | 2.70 | >4.32 | >4.32 |
| *Escherichia coli* O:157H:7 (ATCC 43888) | 2.51 | >4.98 | 0.96 | 2.71 | 0.45 | 1.29 | 2.29 | >4.98 | 1.32 | 2.65 | >4.22 | >4.22 |
| *Citrobacter freundii* (ATCC 43864) | 3.46 | >4.88 | 0.64 | 1.56 | 0.97 | 1.50 | 4.66 | >4.88 | 0.44 | 0.61 | >4.28 | >4.28 |
| *Enterococcus faecium* (ATCC 51559) | 3.37 | 4.26 | 0.53 | 1.38 | 0.32 | 0.72 | 2.67 | 4.05 | 0.72 | 1.95 | 0.30 | 0.54 |
| *Enterococcus faecalis* (ATCC 51299) | >5.98 | >5.98 | 0.78 | 2.30 | 1.08 | 2.06 | 4.23 | 5.41 | 1.08 | 2.38 | 0.75 | 1.20 |
| *Clostridium difficile* (ATCC 9689) | 3.44 | 3.56 | >4.14 | >4.14 | >4.14 | >4.14 | >4.14 | >4.14 | >4.14 | >4.14 | >4.14 | >4.14 |
| *Candida albicans* (ATCC 10231) | 1.78 | 3.05 | 0.44 | 1.08 | 0.09 | 0.33 | 0.20 | 1.08 | 0.37 | 0.83 | 2.07 | 2.63 |
| *Candida tropicalis* (ATCC 750) | 2.01 | 2.85 | 1.12 | 2.12 | 0.25 | 0.42 | 0.28 | 0.79 | 1.32 | 2.36 | >4.36 | >4.76 |
| *Shodotorula rubra* (ATCC 9449) | >5.14 | >5.14 | 2.05 | 2.68 | 2.60 | 4.32 | 4.91 | >5.14 | 2.52 | 3.33 | >4.74 | >4.74 |

Time Kill Summary-II @ 30 seconds

| | Composition A | Formula AA-1 [1)] | Retail-CS (nonmed.) |
|---|---|---|---|
| | 19 organisms > 3 log or 99.9% | 16 > 3 log | 2 > 3 log |
| | 2 organisms > 2 log or 99% | 2 > 2 log | 0 > 2 log |
| | 2 organisms > 1 log or 90% | 1 > 1 log | 1 > 1 log |
| | 1 organism < 1 log | 0 < 1 log | 16 < 1 log |
| | HCPHW-I | HCPHW-J | Retail-EAB |

Time Kill Summary-II @ 30 seconds

| | | | |
|---|---|---|---|
| 16 organisms > 3 log or 99.9% | 8 > 3 log | 1 > 3 log |
| 4 organisms > 2 log or 99% | 2 > 2 log | 2 > 2 log |
| 2 organisms > 1 log or 90% | 2 > 1 log | 1 > 1 log |
| 2 organisms < 1 log | 7 < 1 log | 15 < 1 log |
| HCPHW-G | Retail-SAB | Retail-SSA |
| 10 organisms > 3 log or 99.9% | 5 > 3 log | 1 > 3 log |

-continued

| Time Kill Summary-II @ 30 seconds | | |
| --- | --- | --- |
| 5 organisms > 2 log or 99% | 1 > 2 log | 2 > 2 log |
| 1 organism > 1 log or 90% | 1 > 1 log | 1 > 1 log |
| 8 organisms < 1 log | 12 < 1 log | 15 < 1 log |

| HCPHW-H | Retail-KAB | Retail-SSM (nonmed.) |
| --- | --- | --- |
| 9 organisms > 3 log or 99.9% | 3 > 3 log | 1 > 3 log |
| 2 organisms > 2 log or 99% | 1 > 2 log | 0 > 2 log |
| 5 organisms > 1 log or 90% | 6 > 1 log | 1 > 1 log |
| 8 organisms < 1 log | 9 < 1 log | 17 < 1 log |

| HCPHW-E | Retail-PAB | Retail-ILS (nonmed.) |
| --- | --- | --- |
| 7 organisms > 3 log or 99.9% | 3 > 3 log | 1 > 3 log |
| 3 organisms > 2 log or 99% | 1 > 2 log | 1 > 2 log |
| 3 organisms > 1 log or 90% | 5 > 1 log | 1 < 1 log |
| 11 organisms < 1 log | 10 < 1 log | 16 < 1 log |

| HCPHW-F | Retail-SSP | |
| --- | --- | --- |
| 7 organisms > 3 log or 99.9% | 2 > 3 log | |
| 1 organism > 2 log or 99% | 1 > 2 log | |
| 3 organisms > 1 log or 90% | 1 > 1 log | |
| 13 organisms < 1 log | 15 < 1 log | |

[1] FORMULA AA-1 is a retail antibacterial formula produced in accordance with U.S. Pat. No. 6,107,261.

EXAMPLE 10

Antimicrobial Performance Tests (Health Care Personnel Hand Wash Test)—The FDA issued a tentative final monograph (Jun. 17, 1994) setting forth a health care personnel hand wash method to determine the effectiveness of antibacterial cleansing products. The following embodiment of the present invention was tested using this method:

Composition B (by weight): 0.04 TCS/5DPG/15SXS/0.75ALS/0.75CAPB/0.129 Disodium Phosphate/0.066 Citric Acid, buffer (pH≅6)/0.1 Cetyl Alcohol/0.05 fragrance/1.0 Sodium PCA/2.97GLY/0.25 Polyquaternium-10/0.1 Aloe Vera Gel/0.15 Methyl Paraben/0.05 Propylparaben/0.00005 FD&C Red #4/0.000025 Yellow #5.

The in-use antibacterial efficacy of Composition B was determined by a health care personnel hand wash study. The study was performed according to the current revision of ASTM E-1174-00, *Standard Test Method for Evaluation of the Effectiveness of Health Care Personnel or Consumer Hand wash Formulations*, incorporated herein by reference. The revision to the test method provides procedures to assure adequate rapid neutralization of the antimicrobial in the hand wash formulation. A neutralizer was incorporated at both sampling points. The study is designed to measure the reduction of transient microbial flora following routine hand washing with an antibacterial product. In this study, a broth culture of *Serratia marcescens* ATCC$_{14756}$ was used as an artificial contaminant bacteria on the hands. Activity was measured by comparing the microbial counts of the marker organism removed after a single use of the test composition to the baseline number, i.e., the number of organisms recovered from contaminated, unwashed hands. Additional comparisons were made following the tenth wash of a multiple wash procedure.

Prior to each of the eleven washes, the hands were artificially contaminated with *S. marcescens*. In addition to testing Composition B, HCPHW-I also was included in the study. A sufficient number of subjects fulfilling the study criteria were preenrolled to ensure the required number of subjects (45), 30 for Composition B and 15 for HCPHW-I. During a one-week wash out period, the subjects refrained from using antimicrobial-containing products. On the test day, subjects' hands were contaminated with *S. marcescens* and a baseline sampling was performed. Following washing with the test composition, and following treatments 1 and 10, the subjects' hands were sampled for a post-treatment count. The sampling fluid was enumerated for recovery of *S. marcescens*. Results from the Health Care Personnel Hand Wash study were evaluated by comparing bacteria counts recovered from the hands following product treatment vs. the baseline counts. The bacteria counts were converted into $\log_{10}$ counts. The log counts of each subject's left and right hand were averaged. The following $\log_{10}$ reductions were observed:

| Product Description | WASH 1 | WASH 10 |
| --- | --- | --- |
| Composition B | 3.47 | 3.58 [2] |
| HCPHW-I | 2.50 | 3.78 [2] |

[2] No statistical difference between the test compositions.

For antiseptic hand wash or health care personnel hand wash products, as proposed in the Tentative FDA Monograph (Health care Antiseptic Drug Products), the following criteria should be met: a 2 log reduction of the marker organism on each hand within 5 minutes after the first wash and a 3 log reduction of the marker organism on each hand within 5 minutes following the tenth wash.

Composition B met and surpassed both of these criteria. When compared to HCPHW-I, Composition B performed significantly better with respect to reducing the concentration of the marker organism after one wash, and was equally effective following the tenth wash. The demonstrated log reductions illustrate that the present compositions are effective as Health Care Personnel Hand wash products.

EXAMPLE 11

Repeat Application Soap Chamber Test—A soap chamber irritation test was performed to determine the mildness of Composition A vs. several commercially available Health Care Personnel Hand Wash products. The tests showed that: (a) all test compositions were significantly less irritating than the positive control, i.e., a dilute solution of sodium lauryl sulfate (SLS), and (b) ranking products from highest irritation potential to lowest is: SLS>HCPHW-E>HCPHW-H>HCPHW-G>HCPHW-F>Composition A>Negative Control.

Methodology

Twelve male and female subjects between the ages of 18 and 65, who were in good health, were enrolled in the test. Dilute solutions of all test compositions were made each day of patching. Patches were totally occlusive chambers, 12 mm in diameter, applied to the volar forearm for a total of six days. Expert visual gradings, using a four-point scale for erythema, scaling, and fissuring were used as the objective measure of observation for this study. Grading was performed at baseline (i.e., when panelists were enrolled), 30 minutes after patch removal on days one to six, and at 24 hours on days one to six. A maximum for each tested characteristic was established as a "3" score.

Summary

The rating for the commercially available hand wash products, from highest irritation potential to the lowest, was:

Positive Control>HCPHW-E>HCPHW-H>HCPHW-G>HCPHW-F>Composition A>Negative Control. Significant differences were noted overall between HCPHW-E and HCPHW-H, compared to HCPHW-G, HCPHW-F, and Composition A. Directional differences existed between Composition A, HCPHW-F, and HCPHW-G, with Composition A demonstrating the lowest irritation potential as measured under the conditions of the test.

TABLE 1

Professional Products Statistical Groupings

| Product | Mean Summary Score | Statistical Grouping | | | |
|---|---|---|---|---|---|
| Positive Control | 11.8 | I | | | |
| HCPHW-E | 3.9 | | II | III | |
| HCPHW-H | 2.2 | | II | III | IV |
| HCPHW-G | 1.3 | | | III | IV | V |
| HCPHW-F | 1.0 | | | | IV | V |
| Composition A | 0.9 | | | | IV | V |
| Negative Control | 0.0 | | | | | V |

EXAMPLE 12

Occupational Hand Wash Study (Health care Personnel)—The following embodiment of the present invention was used in this test:

Composition C (by weight): 0.40 TCS/5DPG/15SXS/0.75ALS/0.75CAPB/0.129 Disodium Phosphate/ 0.066 Citric Acid, buffer (ph≅6)/0.1 Cetyl Alcohol/0.05 fragrance/1 Sodium PCA/2.97GLY/0.25 Polywaternium-100/0.1 Aloe Vera Gel/0.00005 FD&C Red #4/0.000025 Yellow #5.

Composition C was tested vs. commercially available HCPHW-E in an occupational hand wash study. It is expected that a health care worker would have a greater exposure over an extended time period to a hand wash than the general public. Accordingly, this test was designed to mimic the population demographics and hand wash patterns likely to be encountered in a health care setting. HCPHW-E was selected based on its prior acceptance in the health care industry as being an efficacious and mild health care personnel hand wash.

Methodology

The study demographics were selected to mimic a population cross section encountered in a health care setting. Thirty-eight volunteers, who were in good general health, participated in the study. The panel included nine volunteers with clinically assessed "dry skin," and twenty-nine volunteers with clinically assessed "normal skin." These determinations were made by an expert grader following a two-week preconditioning period during which all volunteers washed with a commercially available mild skin care soap bar and discontinued the use of all topically applied moisturizers, creams, lotions, and antibacterial products. Each panelist was qualified for participation after the two-week preconditioning period. The age range of the panelists was between 20 and 55 years of age, and the sex distribution was three males and thirty-five females.

The test compositions were coded and sent to an independent laboratory for testing. The test was a single-blind study in which only the wash monitors were aware of the coded product assignments when the products were applied to the hand and volar forearm. All wash procedures were conducted in a separate area in order to maintain blinding of the expert grader and instrument operators. The test materials were dispensed by a wash monitor into the hand of the panelists during the wash procedure.

Using appropriate randomization, panelists were assigned a wash partner for "skin-to-skin" friction. Composition C was applied to dry skin and spread over the hand and forearm for 30 seconds. Immediately thereafter, the panelists were instructed to rinse the hand and forearm for 15 seconds. The skin was patted dry with a disposable towel. HCPHW-E was applied to wetted skin and spread over the designated hand and forearm for 30 seconds. Immediately following, panelists were instructed to rinse the hand and forearm for 15 seconds. The skin was patted dry with a disposable towel. The time between wash cycles was approximately five minutes. The time between the tenth cycle and grading was approximately twenty minutes. These protocols were chosen to represent typical in-use scenarios envisioned for both samples used as commercial products.

To determine the effects that the two test compositions had on panelists' skin, both visual expert grading and instrumental evaluations were used. Expert grading involved the "Dryness," "Erythema," and "Tactile Roughness" scales summarized below. Base line expert gradings and instrumental measurements were taken between the start of the first wash cycle on day one. Each panelist was graded, then participated in ten (10) wash cycles in the morning, graded again, and then subjected to ten (10) wash cycles in the afternoon. Instrumental measurements were taken at termination of use of a composition, or at completion of the study.

Dryness

0 = None
1 = Slight flaking or occasional small lifting of scales
2 = Moderate flaking/scaling
3 = Marked scaling/slight fissuring, cracking, lifting of scales
4 = Severe scaling, cracking, and fissuring Erythema 0 = None
1 = Mild diffuse erythema, limited to a small area
2 = Moderate pinkness, more extensive area
3 = Marked erythema, may include deeper areas of erythema/slight edema
4 = Severe erythema, or presence of edema, fissuring, possible erosions Tactile Roughness 0 = Normal
1 = Slight roughness
2 = Moderate roughness
3 = Severe roughness
4 = Extreme roughness At the end of the study, the subjects completed a questionnaire directed to their perception of dryness, tightness, itching, and burning for each hand/arm. The scale used for rating was:

Self-assessment

| No dryness | 0 | 1 | 2 | 3 | 4 severe dryness |
| No tightness | 0 | 1 | 2 | 3 | 4 severe tightness |
| No itching | 0 | 1 | 2 | 3 | 4 severe itching |
| No burning/soreness | 0 | 1 | 2 | 3 | 4 severe burning/soreness |

Results

The tests used in this study are summarized in the following table.

| | |
|---|---|
| Observation of number of panelists able to complete test | indicates panelists' ability to tolerate composition in high use situation; more panelists able to complete test = milder product |
| Visual Expert Grading | dryness, erythema, roughness; lower reading = milder product |
| Panelist Self-assessment | perception of dryness, tightness, itching, burning/soreness; lower reading = milder product |
| Minolta Chromameter | instrumental reading of skin redness; lower reading = skin less irritated |
| Transepidermal Water Loss (TEWL) | instrumental assessment of skin barrier function; lower reading = less damage to skin barrier function |

Number of Panelists Able to Complete Test

Figure 1B:
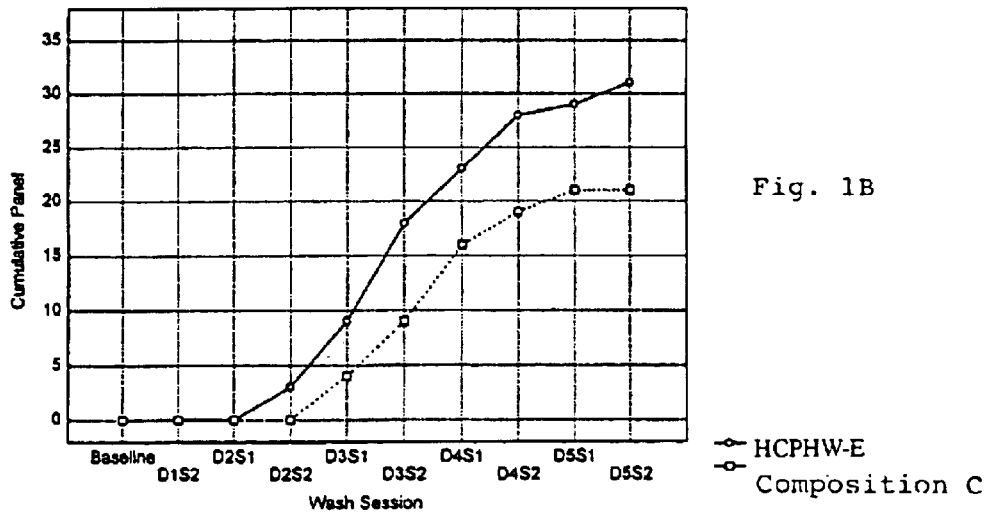

The number of panelists able to complete all washings was significantly greater with Composition C than with HCPHW-E. In addition, the total number of washings completed without significant redness, dryness, and roughness was higher for Composition C than for HCPHW-E. Less dryness and redness was observed on forearms washed with Composition C than forearms washed with HCPHW-E. These results are illustrated in the graphs of FIG. 1A and FIG. 1B.

Visual Expert Grading

Expert Grader Evaluations were performed using a four-point scale on panelist dorsal hands, webbing of fingers, and volar forearms for qualitative measurements of dryness, erythema (redness), and tactile roughness. The "Total Panel" consisted of all panelists, i.e., those with normal skin and with dry skin. Less dryness and redness were observed on forearms washed with Composition C than those washed with HCPHW-E. For dry skin subjects, the expert grader assessed determined that the panel experienced less redness while using Composition C was used. The results are illustrated in the following two tables.

| | Expert Grader Assessment of Total Panel | | | | | |
|---|---|---|---|---|---|---|
| | Webbing of Fingers Composition C | Webbing of Fingers HCPHW-E | Dorsal Hand Composition C | Dorsal Hand HCPHW-E | Volar Forearms Composition C | Volar Foreamrs HCPHW-E |
| Dryness | | | | | | |
| Mean | 1.2 | 1.0 | 1.2 | 1.0 | 1.0 | 1.1 |
| Standard Deviation | 0.9 | 0.7 | 0.8 | 0.8 | 0.7 | 0.7 |
| Paired T-Test | 0.35 | | 0.34 | | 0.81 | |
| Roughness | | | | | | |
| Mean | 1.9 | 1.5 | 1.7 | 1.5 | 1.1 | 1.1 |
| Standard Deviation | 0.7 | 0.7 | 0.8 | 0.7 | 0.4 | 0.4 |
| Paired T-Test | 0.00 | | 0.01 | | 0.86 | |
| Erythema | | | | | | |
| Mean | 1.0 | 1.1 | 1.6 | 1.6 | 2.1 | 2.8 |
| Standard Deviation | 0.6 | 0.7 | 0.6 | 0.5 | 0.9 | 0.6 |
| Paired T-Test | 0.45 | | 0.45 | | 0.00 | |

| | Expert Grader Assessment of Panelists with Dry Skin (Termination and EndPoint Scores) | | | | | |
|---|---|---|---|---|---|---|
| | Webbing of Fingers Composition C | Webbing of Fingers HCPHW-E | Dorsal Hand Composition C | Dorsal Hand HCPHW-E | Volar Forearms Composition C | Volar Forearms HCPHW-E |
| Dryness | | | | | | |
| Mean | 1.2 | 0.2 | 1.4 | 1.5 | 1.0 | 1.0 |
| Standard Deviation | 0.54 | 0.53 | 0.77 | 1.2 | 1.0 | 0.74 |
| Paired T-Test | 0.02 | | 0.97 | | 0.95 | |
| Roughness | | | | | | |
| Mean | 1.9 | 1.9 | 2.3 | 2.3 | 1.1 | 1.1 |
| Standard | 0.46 | 0.38 | 0.65 | 0.36 | 0.51 | 0.49 |

-continued

| Expert Grader Assessment of Panelists with Dry Skin (Termination and EndPoint Scores) | | | | | | |
|---|---|---|---|---|---|---|
| | Webbing of Fingers Composition C | Webbing of Fingers HCPHW-E | Dorsal Hand Composition C | Dorsal Hand HCPHW-E | Volar Forearms Composition C | Volar Forearms HCPHW-E |
| Deviation | | | | | | |
| Paired T-Test | 0.86 | | 0.63 | | 1.0 | |
| Erythema | | | | | | |
| Mean | 1.0 | 1.1 | 1.4 | 2.0 | 1.9 | 2.8 |
| Standard Deviation | 0.46 | 0.60 | .049 | 0.78 | 0.98 | 0.51 |
| Paired T-Test | 0.12 | | 0.10 | | 0.04 | |

Panelist Self-Assessment

Panelist perception of the test compositions was obtained at the end of the study. The scale used by the subjects to assess the composition as set forth in the methodology section. Panelists were asked to rank their overall impression of the two test composition for four characteristics: dryness, tightness, itching, and burning. The perception for the total panel ranked Composition C as being significantly less drying and experiencing significantly less tightness, less itching sensation, and less burning than HCPHW-E. The results are summarized in the following tables.

were taken. Chromameter values at end-point and termination show that Composition C is significantly less irritating the HCPHW-E. The results are summarized in FIG. 2.

Transepidermal Water Loss (TEWL)

Transepidermal Water Loss (TEWL) values for the total panel, at termination of the test, demonstrate that Composition C causes significantly less damage to the skin surface than HCPHW-E. Normally, the skin surface has barrier functions, both protecting from external influences and preserving internal balances. TEWL is a measurement that quantifies the amount of water escaping from the skin

| Self-Assessment at End of Study | | | | | | | | |
|---|---|---|---|---|---|---|---|---|
| | Dryness Composition C | Dryness HCPHW-E | Tightness Composition C | Tightness HCPHW-E | Itching Composition C | Itching HCPHW-E | Burning Composition C | Burning HCPHW-E |
| Mean | 2.1 | 2.6 | 2.1 | 2.7 | 1.3 | 2.2 | 1.7 | 2.9 |
| Std. Dev. | 1.1 | 1.3 | 1.2 | 1.2 | 1.2 | 1.3 | 1.4 | 1.3 |
| Paired T-test | 0.0039 | | 0.0056 | | 0.0002 | | 0.0000 | |

| Self-Assessment at End of Study (Dry Skin Panelists Only) | | | | | | | | |
|---|---|---|---|---|---|---|---|---|
| | Dryness Composition C | Dryness HCPHW-E | Tightness Composition C | Tightness HCPHW-E | Itching Composition C | Itching HCPHW-E | Burning Composition C | Burning HCPHW-E |
| Mean | 2.3 | 2.4 | 2.1 | 2.3 | 1.8 | 2.1 | 1.8 | 2.8 |
| Std. Dev. | 0.7 | 1.2 | 1.2 | 1.4 | 1.2 | 1.8 | 1.4 | 1.3 |
| Paired T-test | 0.799 | | 0.729 | | 0.594 | | 0.067 | |

Minolta Chromameter

A Minolta Chromameter was used to quantify the change in surface redness of skin exposed to the wash cycles on both the dorsal hand and volar forearm surface. Measurements are taken along a red color spectrum, with increasing irritation represented by increasing redness along the color spectrum. Both the dorsal hand and volar forearm measurements were consistent with the Expert Grader assessments. The dorsal hand surface was significantly less red for sites washed with Composition C than sites washed with HCPHW-E. The volar forearm demonstrated an even greater difference between sites washed with Composition C and HCPHW-E. In particular, Composition C exhibited very minor changes in redness at the sites where measurements surface as a result of damage due to washing with a surfactant. Composition C produced significantly less damage to the skin surface, when quantified by water loss, than HCPHW-E on both the dorsal hand and volar forearm. The results are summarized in FIG. 3.

Summary

Under the conditions used in this example, Composition C is milder than HCPHW-E. Total panel self-assessments reported experiencing less dryness, tightness, itching, and burning when using Composition C. For dry skin subjects, expert grader assessments determined that the panel experienced less redness when using Composition C, and a greater ability to complete more washes when using Composition C. Dry skin panelists in the self-assessments, also reported experiencing less dryness, tightness, itching, and burning when using Composition C. Instrumental assessments for the whole panel significantly favored Composition C because of imparting significantly less damage to skin functions than HCPHW-E.

The examples show the unexpected benefits achieved by compositions of the present invention. The data presented above illustrate that a present antibacterial composition can contain ingredients to enhance product esthetics and to impart skin care properties, and can exhibit a log reduction of at least about 2 (after 30 seconds) or at least about 3 (after 60 seconds) vs. S. aureus, or of at least about 2.5 (after 30 seconds) or at least about 3.5 (after 60 seconds) vs. E. coli.

The antibacterial compositions of the present invention have several practical end uses, including hand cleansers, mouthwashes, surgical scrubs, body splashes, hand sanitizer gels, and similar personal care products. Additional types of compositions include foamed compositions, such as creams, mousses, and the like, and compositions containing organic and inorganic filler materials, such as emulsions, lotions, creams, pastes, and the like. The compositions further can be used as an antibacterial cleanser for hard surfaces, for example, sinks and countertops in hospitals, food service areas, and meat processing plants. The present antibacterial compositions can be manufactured as dilute ready-to-use compositions, or as concentrates that are diluted prior to use. The compositions can be applied to a surface, then either rinsed from, wiped from, or allowed to remain on the treated surface.

The compositions also can be incorporated into a web material to provide an antibacterial wiping article. The wiping article can be used to clean and sanitize skin or inanimate surfaces.

The present antimicrobial compositions provide the advantages of a broad spectrum kill of Gram positive and Gram negative bacteria in short contact times. The short contact time for a substantial log reduction of bacteria is important in view of the typical 15 to 60 second time frame used to cleanse and sanitize the skin and inanimate surfaces.

The present compositions are effective in short contact time because the antibacterial agent is present in the aqueous continuous phase of the composition, as opposed to surfactant micelles. The antibacterial agent, therefore, is available to immediately begin reducing bacterial populations, and further is available to deposit on the skin to provide residual antibacterial efficacy. In addition, because the antibacterial agent is in solution as opposed to surfactant micelles, the absolute amount of antimicrobial agent in the composition can be reduced without adversely affecting efficacy, and the antibacterial agent is not rinsed from the skin with the surfactant prior to performing its antibacterial function. In addition, the amount of surfactant in the present antibacterial compositions typically is low, thereby providing additional environmental benefits. Furthermore, the present compositions exhibit excellent esthetic properties, especially with respect to foam generation and foam stability, making the compositions useful in pump foam dispersers.

Obviously, many modifications and variations of the invention as hereinbefore set forth can be made without departing from the spirit and scope thereof, and, therefore, only such limitations should be imposed as are indicated by the appended claims.

APPENDIX A

Skincare Agents

Acetyl Tnoctyl Citrate
Apricot Kernel Oil PEG-6 Esters
Butyl Acetyl Ricinoleate
Butyl Mynstate
Butyl Oleate
Butyl Stearate
C18-36 Acid Glycol Ester
C12-15 Alcohols Benzoate
C12-15 Alcohols Lactate
C12-15 Alcohols Octanoate
C15-18 Glycol
C18-20 Glycol Isostearate
C14-16 Gylcol Palmrtate
C11-15 Pareth-3 Oleate
C11-15 Pareth-3 Stearate
C11-15 Pareth-12 Stearate
C12-15 Pareth-9 Hydrogenated Tallowate
C12-15 Pareth-12 Oleate
Caprylic/Capnc/Diglyceryl Succinate
Caprylic/Capnc Glycendes
Carpylic/Capnc/Isosteanc/Adipic Triglycendes
   Cetyl Acetate
   Cetylarachidol
   Cocoglycendes
Corn Oil PEG-6 Esters
Cottonseed Glycende
Dibutyl Adipate
Dibutyl Sebacate
Di-C12-15 Alcohols Adipate
Dicapryl Adipate
Dicetyl Adipate
Diethylene Glycol Dibenzoate
Diethyl Palmrtoyl Aspartate
Diethyl Sebacate
Dihexyl Adipate
Dihydrocholesteryl Octyldecanoate
Dihydrophytosteryl Octyldecanoate
Dihydroxyethyl Soyamine Dioleate
Dihydroxyethyl Tallowamine Oleate
Diisobutyl Adipate
Diisocetyl Adipate
Diisodecyl Adipate
Diisopropyl Adipate
Diisopropyl Diinoleate
Diisopropyl Sebacate
Dipropylene Glycol Dibenzoate
Ditndecyl Adipate
Ethyl Arachidonate
Ethyl Laurate
Ethyl Linoleate
Ethyl Linolenate
Ethyl Morrhuate
Ethyl Mynstate
Ethyl Palmrtate
Ethyl Pelargonate
Ethyl Persate
Ethyl Stearate
Fish Glycendes
Glyceryl Benenate
Glyceryl Caprate
Glyceryl Caprylate
Glyceryl Caprylate/Caprate
Glyceryl Cocoate Glyceryl Dilaurate
Glyceryl Dioleate
Glyceryl Distearate
Glyceryl Erucate
Glyceryl Hydroxystearate
Glyceryl Isostearate
Glyceryl Lanolate
Glyceryl Laurate
Glyceryl Linoleate
Glyceryl Mynstate
Glyceryl Oleate
Glyceryl Palmrtate Lactate
Glyceryl Ricinoleate
Glyceryl Sesquioleate
Glyceryl Stearate
Glyceryl Stearate Citrate
Glyceryl Stearate Lactate
Glyceryl Triacetyl Hydroxystearate
Glyceryl Triacetyl Ricinoleate
Glyceryl Trioctanoate
Glyceryl Triundecanoate
Glyceryl Dioctanoate
Glyceryl Hydroxystearate
Glycol Oleate
Glycol Ricinoleate
Glycol Stearate
Heptylundecanol
Hexyl Laurate
Hydrogenated Coco-Glycendes
Hydrogenated Lard Glycende
Hydrogenated Lard Glycendes
Hydrogenated Palm Glycendes
Hydrogenated Palm Kernal Glycendes
Hydrogenated Palm Oil Glycende
Hydrogenated Palm Oil Glycendes
Hydrogenated Palm/Palm Kernel Oil PEG-6 Esters
Hydrogenated Polyisobutene
Hydrogenated Soybean Oil Glycendes
Hydrogenated Soy Glycende
Hydrogenated Tallow Glycende
Hydrogenated Tallow Glycende Citrate
Hydrogenated Tallow Glycende Lactate
Hydrogenated Tallow Glycendes
Hydrogenated Tallow Glycendes Citrate
Hydrogenated Vegetable Glycende
Hydrogenated Vegetable Glycendes
Hydrogenated Vegetable Glycendes Phosphate
Hydroxylated Lanolin
Hydroxyoctacosanyl Hydroxystearate
Isoamyl Laurate
Isobutyl Mynstate
Isobutyl Palmrtate
Isobutyl Pelargonate
Isobutyl Stearate
Isohexyl Laurate
Isohexyl Palmrtate
Isopropyl Isostearate
Isopropyl Lanolate
Isopropyl Laurate
Isopropyl Linoleate
Isopropyl Methoxycinnamate
Isopropyl Mynstate
Isopropyl Oleate
Isopropyl Palmrtate
Isopropyl Ricinoleate
Isopropyl Stearate
Isopropyl Tallowate Isostearyl Alcohol
Isostearyl Benzoate
Isostearyl Isostearate
Isostearyl Lactate
Isostearyl Neopentanoate
Isostearyl Palmrtate
Isotndecyl Isononanoate
Laneth-9 Acetate
Laneth-10 Acetate
Lanolin
Lard Glycendes
Laureth-2 Benzoate
Lauryl Isostearate
Lauryl Lactate
Methyl Acetyl Ricinoleate
Methyl Caproate
Methyl Caprylate
Methyl Caprylate/Caprate
Methyl Cocoate
Methyl Dehydroabietate
Methyl Glucose Sesquioleate
Methyl Glucose Sesquistearate
Methyl Hydrogenated Rosinate
Methyl Hydroxystearate
Methyl Laurate
Methyl Linoleate
Methyl Mynstate
Methyl Oleate
Methyl Palmrtate
Methyl Pelargonate
Methyl Ricinoleate
Methyl Rosinate
Methyl Stearate
Myreth-3 Caprate
Myreth-3 Laurate
Myreth-3 Mynstate
Myreth-3 Palmrtate
Neopentyl Glycol Dicaprate
Neopenytl Glycol Dioctanoate
Nonyl Acetate
Octyl Acetoxystearate
Octyldodecyl Neodecanoate
Octyl Hydroxystearate
Octyl Isononanoate
Palm Kernel Glycendes
Palm Oil Glycendes
PEG-6 Caprylic/Capnc Glycendes
PEG-2 Castor Oil
PEG-3 Castor Oil
PEG-4 Castor Oil
PEG-5 Castor Oil
PEG-8 Castor Oil
PEG-9 Castor Oil
PEG-10 Castor Oil
PEG-10 Coconut Oil Esters
PEG-5 Glyceryl Trisostearate
PEG-5 Hydrogenated Castor Oil
PEG-7 Hydrogenated Castor Oil
PEG-5 Hydrogenated Corn Glycendes
PEG-5 Hydrogenated Fish Glycendes
PEG-20 Methyl Glucose Sesquinstearate
Pentaerythntyl Rosinate
Pentaerythntyl Tetraoctanoate
Pentaerythntyl Tetraoleate
PPG-4-Ceteth-1
PPG-8-Ceteth-1
PPG-8-Ceteth-2

PPG-10 Cetyl Ether
PPG-10 Cetyl Ether Phosphate
PPG-28 Cetyl Ether
PPG-30 Cetyl Ether
PPG-50 Cetyl Ether
PPG-17 Dioleate
PPG-3 Hydrogenated Castor Oil
PPG-30 Isocetyl Ether
PPG-5 Lanolate
PPG-2 Lanolin Alcohol Ether
PPG-5 Lanolin Alcohol Ether
PPG-10 Lanolin Alcohol Ether
PPG-20 Lanolin Alcohol Ether
PPG-30 Lanolin Alcohol Ether
PPG-5 Lanolin Wax
PPG-5 Lanolin Wax Glcende
PPG-9 Laurate
PPG-4 Lauryl Ether
PPG-3 Mynstyl Ether
PPG-4 Mynstyl Ether
PPG-26 Oleate
PPG-36 Oleate
PPG-10 Oleyl Ether
PPG-20 Oleyl Ether
PPG-23 Oleyl Ether
PPG-30 Oleyl Ether
PPG-37 Oleyl Ether
PPG-50 Oleyl Ether
PPG-9-Steareth-3
PPG-11 Stearyl Ether
PPG-15 Stearyl Ether
Propylene Glycol Isostearate
Propylene Glycol Hydroxystearate
Propylene Glycol Laurate
Propylene Glycol Mynstate
Propylene Glycol Mynstyl Ether
Propylene Glycol Mynstyl Ether Acetate
Propylene Glycol Oleate
Propylene Glycol Ricinoleate
Propylene Glycol Soyate
Propylene Glycol Stearate
Soy Sterol
Soy Sterol Acetate
Squalene
Stearoxytnmethylsriane
Sucrose Distearate
Suffunzed Jojoba Oil
Sunflower Seed Oil Glycendes
Tall Oil Glycendes
Tallow Glycende
Tallow Glycendes
Trisocetyl Citrate
Trisosteann PEG-6 Esters
Trimethylsilylamodimethicone
Triolein PEG-6 Esters
Tris(Tributoxysiloxy)Methylsilane
Vegetable Glycendes Phosphate
Wheat Germ Glycendes
Adenosine Phosphate
Adenosine Triphosphate
Alanine
Aldioxa
Allantoin Ascorbate
Allantoin Biotin
Allantoin Calcium Pantothenate
Allantoin Galacturonic Acid
Allantoin Glycyrrhetinic Acid
Allantoin Polygalacturonic acid
Aloe
Animal Collagen Amino Acids
Animal Elastin Amino Acids
Animal Keratin Amino Acids
Arginine
Asparagine
Aspartic Acid
Camphor
Caprylyl/Capryl Glucoside
Casein
Cetyl Cetaine
Chlorodeceth-14
Cholesterol
Cocamidopropyl Lauryl Ether
Cysteine
Cysteine HCl
Cystine
Desamido Animal Collagen
Dicaprytoyl Cystine
Diethyl Aspartate
Diethylene Tricaseinamide
Diethyl Glutamate
Dihydrocholesterol
Dipalmitoyl Hydroxyproline
Disodium Adenosine Triphosphate
Ethyl Aspartate
Ethyl Ester of Hydrolyzed Animal Protein
Ethyl Glutamate
Ethyl Sennate
Ethyl Urocanate
Folic Acid
Frutose
Glutamic Acid
Glutamine
Glyceryl Lanolate
Glycine
Glycogen
Guanosine
Hexamethyldisiloxane
Hexyl Nicotinate
Histidine
Human Placental Protein
Hyaluronic Acid
Hydrogenated Animal Glycende
Hydrogenated Laneth-5
Hydrolyzed Animal Elastin
Hydrolyzed Animal Keratin
Hydrolyzed Animal Protein
Hydrolyzed Casein
Hydrolyzed Human Placental Protein
Hydrolyzed Mucopolysacchandes
Hydrolyzed Silk
Hydrolyzed Soy Protein
Hydrolyzed Vegetable Protein
Hydrolyzed Yeast Protein
Hydrolyzed Lanolin
Hydroxyproine
Isoleucine
Keratin
Laneth-4 Phosphate
Laneth-5
Lanolinamide DEA
Lanosterol
Lard Glycendes
Lauramidopropyl Betaine
Lauryl Aminopropylglycine Lauryl Diethylenediaminoglycine
Lecithin
Leucine
Lysine
Magnesium Aspartate
Magnesium Lanolate
MEA-Hydrolyzed Animal Protein
Methionine
2-Methyl-4-Hydroxypyrrolidine
Milk
Mixed Isopropanolamines Lanolate
Mixed Mucopolysacchandes
Monosacchande Lactate Condons
Niacinamide
Norvaine
Oleyl Betane
θrotic Acid
Palmitoyl Animal Collagen Amino Acids
PEG-5 Hydrogenated Lanolin
PEG-10 Hydrogenated Lanolin
PEG-2 Milk Solids
PEG-6 Soya Sterol Undecylenate
Phenytalanine
Polyglyceryl-2 Lanolin Alcohol Ether
Potassium Aspartate
Potassium Caseinate
Potassium DNA
PPG-2Buteth-3
PPG-3Buteth-5
PPG-5Buteth-7
PPG-7Buteth-10
PPG-9Buteth-12
PPG-12Buteth-16
PPG-15Buteth-20
PPG-20Buteth-30
PPG-24Buteth-27
PPG-25Buteth-26
PPG-28Buteth-35
PPG-33Buteth-45
PPG-4 Butyl Ether
PPG-5 Butyl Ether
PPG-9 Butyl Ether
PPG-14 Butyl Ether
PPG-15 Butyl Ether
PPG-16 Butyl Ether
PPG-18 Butyl Ether
PPG-22 Butyl Ether
PPG-24 Butyl Ether
PPG-30 Butyl Ether
PPG-33 Butyl Ether
PPG-40 Butyl Ether
PPG-53 Butyl Ether
PPG-2 Isostearate
PPG-10 Methyl Glucose Ether
PPG-20 Methyl Glucose Ether
PPG-20 Methyl Glucose Ether Acetat
PPG-2 Mynstyl Ether Propionate
Pregnenolone Acetate
Proline
Pyndoxine
Pyndoxine Dicaprylate
Pyndoxine Dilaurate
Pyndoxine Dioctenoate
Pyndoxine Dipalmitate
Pyndoxine HCl
Pyndoxine Tripalmitate
Resorcinol Acetate
Retnol
Retinyl Acetate
Retinyl Palmrtate
Ribonucleic Acid
Ricinoleamidopropyl Betaine
Salicylic Acid
Senine
Serum Albumin
Serum Proteins
Silk Amino Acids
Sodium Caseinate
Sodium Chondroitin Sulfate
Sodium DNA
Sodium Gluconate
Sodium Glutamate
Sodium Hyaluronate
Sodium Lactate Methylsilanol
Sodium Laneth Sulfate
Sodium Mannuronate Methylsilanol
Sodium PCA Methylsilanol
Sodium Riboflavin Phosphate
Sodium Urocanate
Soluble Animal Collagen
Sorbitol
Soyaethyl Morpholinium Ethosulfate
Soy Protein
Sulfunzed Jojoba Oil
Tall Oil Sterol
Thiamine HCl
Thiamine Nitrate
Threonine
Tocopheryl Acetate
Tocopheryl Linoleate
Tocopheryl Nicotinate
Tocopheryl Succinate
Tocopheryl Salicytate
Tridecyl Salicylate
Tridecyl Stearate
Tryptophan
Tyrosine
Unc Acid
Urocanic Acid
Wheat Germamidopropyl Dimethylamine Lactate
Whey Protein
Octylacrylamide/Acrylates/Butylaminoethyl Methacrylate Copolymer
Octylacrylamide/Acrylates Copolymer
PEG-22/Dodecyl Glycol Copolymer
PEG-45/Dodecyl Glycol Copolymer
PEI-7
PEI-15
PEI-30
PEI-45
PEI-275
PEI-700
PEI-1000
PEI-1500
PEI-2500
Polyacrylamide
Polyacrylamidomethylpropane Sulfonic Acid
Polyacrylic Acid
Polyaminopropyl Biguanide
Polyamino Sugar Condensate
Polyquaternium-1
Polyquaternium-2
Polyquaternium-4
Polyquaternium-5

Polyquaternium-6
Polyquaternium-7
Polyquaternium-8
Polyquaternium-9
Polyquaternium-10
Polyquaternium-11
Polyquaternium-12
Polyquaternium-13
Polyquaternium-14
Polyquaternium-15
Polyvinyl Alcohol
Polyvinyl Butyral
Polyvinyl Imidazolinium Acetate
Polyvinyl Laurate
Polyvinyl Methyl Ether
PVM/MA Copolymer
PVP
PVP/Dimethylaminoethylmethacrylate Copolymer
PVP/Ethyl Methacrylate/Methacrylic Acid Copolymer
PVP/Hexadecene Copolymer
Sodium Polystyrene Sulfonate
Sodium Styrene/Acrylate/PEG-10 Dimaleate Copolymer
Starch/Acrylates/Acrylamide Copolymer
Stearylvinyl Ether/Maleic Anhydride Copolymer
Styrene/PVP Colpolymer
Sucrose Benzoate/Sucrose Acetate Isobutyrate/Butyl Benzyl Phthalate Copolymer
Sucrose Benzoate/Sucrose Acetate Isobutyrate/Butyl Benzyl Phthalate/Methyl Methcrylate Copolymer
Sucrose Benzoate/Sucrose Acetate Isobutyrate Coploymer
Meroxapol 105
Meroxapol 108
Meroxapol 171
Meroxapol 172
Meroxapol 174
Meroxapol 178
Meroxapol 251
Meroxapol 252
Meroxapol 254
Meroxapol 255
Meroxapol 258
Meroxapol 311
Meroxapol 312
Meroxapol 314
PEG-4
PEG-6
PEG-8
PEG-9
PEG-10
PEG-12
PEG-14
PEG-16
PEG-18
PEG-20
PEG-32
PEG-40
PEG-6-32
PEG-75
PEG-135
PEG-150
PEG-200
PEG-350
PEG-2M
PEG-5M
PEG-7M
PEG-9M
PEG-14M
PEG-20M
PEG-23M
PEG-45M
PEG-90M
PEG-115M
PEG/PPG-17/6 Copolymer
PEG/PPG-18/4 Copolymer
PEG/PPG-23/50 Copolymer
PEG/PPG-35/9 Copolymer
PEG/PPG-125/30 Copolymer
Poloxamer 101
Poloxamer 105
Poloxamer 108
Poloxamer 122
Poloxamer 123
Poloxamer 124
Poloxamer 181
Poloxamer 182
Poloxamer 183
Poloxamer 184
Poloxamer 185
Poloxamer 188
Poloxamer 212
Poloxamer 215
Poloxamer 217
Poloxamer 231
Poloxamer 234
Poloxamer 235
Poloxamer 237
Poloxamer 238
Poloxamer 282
Poloxamer 284
Poloxamer 288
Poloxamer 331
Poloxamer 333
Poloxamer 334
Poloxamer 335
Poloxamer 338
Poloxamer 401
Poloxamer 402
Poloxamer 403
Poloxamer 407
PPG-9
PPG-12
PPG-15
PPG-17
PPG-20
PPG-26
PPG-30
PPG-34
Acacia
Agar
Algin
Alginic Acid
Ammonium Alginate
Calcium Alginate
Calcium Carrageenan
Callulose Gum
Damar
Dextran
Dextrin
Carboxymethyl Hydroxyethylcellulose
Carboxymethyl Hydroxypropyl Guar
Carrageenan
Ethylcellulose
Gelatin
Guar Gum Guar Hydroxypropyltnmonium Chloride
Gum Benzoin
Hydroxybutyl Methylcellulose
Hydroxyethylcellulose
Hydroxyethyl Ethylcellulose
Hydroxypropylcellulose
Hydroxypropyl Guar
Hydroxypropyl Methylcellulose
Jalap Resin
Karaya Gum
Kelp
Locust Bean Gum
Maltodextnn
Methylcellulose
Ollbanum
Pectin
Potassium Alginate
Potassium Carrageenan
Propylene Glycol Alginate
Sandarac Gum
Sodium Carboxymethyl Dextran
Sodium Carrageenan
Sodium Cellulose Sulfate
Tragacanth Gum
Xanthan Gum
Acrylamides Copolymer
Acrylamide/Sodium Acrylate Copolymer
Acrylate/Acrylamide Copolymer
Acrylate/Ammonium Methacrylate Copolymer
Acrylates Copolymer
Acrylates/Diacetoneacrylamide Copolymer
Acrylates/Steareth-20 Methacrylate Copolymer
Acrylic/Acrylate Copolymer
Adipic Acid/Dimethylaminohydroxypropyl Diethylenetnamine Copolymer
Adipic Acid/Epoxypropyl Diethylenetnamine Copolymer
Allyl Stearate/VA Copolymer
Aminoethylacrylate Phosphate/Acrytate Copolymer
Ammonium Acrylates Copolymer
Ammonium Styrene/Acrylate Copolymer
Ammonium Vinyl Acetate/Acrylates Copolymer
AMP Acrylates/Diacetoneacrylamide Copolymer
AMPD Acrylates/Diacetoneacrylamide Copolymer
Benzoic Acid/Phthalic Anhydride/Pentaerythntol/Neopentyl Glycol/Palmitic Acid Copolymer
Carbomer 910
Carbomer 934
Carbomer 934P
Carbomer 940
Carbomer 941
Corn Starch/Acrylamide/Sodium Acrylate Copolymer
DEA-Styrene/Acrylates/Divinylbenzene Copolymer
Diethylene Glycolamine/Epichlorohydrin/Piperazine Copolymer
Dodecanedioic Acid/Cetearyl Alcohol/Glycol Copolymer
Ethylene Acrylate Copolymer
Hydroxyethyl PEI-1000
Hydroxyethyl PEI-1500
Isobutylene/Maleic Anhydride Copolymer
Isopropyl Ester of PVM/MA Copolymer
Methacryloyl Ethyl Bentaine/Methacrylates Copolymer
Methoxy PEG-22/Dodecyl Glycol Copolymer

What is claimed is:

1. An antibacterial composition comprising:
(a) about 0.001% to about 10%, by weight, of a phenolic antimicrobial agent selected from the group consisting of triclosan, p-chloro-m-xylenol, and mixtures thereof;
(b) about 0.1% to about 40%, by weight, of a surfactant selected from the group consisting of an anionic surfactant, a cationic surfactant, an ampholytic surfactant, and mixtures thereof;
(c) about 1% to about 40%, by weight, of a hydrotrope;
(d) about 1% to about 25%, by weight, of a water-soluble hydric solvent;
(e) about 0.1% to about 3%, by weight, of a skin-care agent selected from the group consisting of a polyvinylpyrrolidone polymer, a protein derivative, a glyceryl ester, an ethoxylated fatty ether, a cellulosic, a derivatized cellulosic, a polyethylene oxide, a cationic quaternary ammonium polymer, N-stearylmorpholine lactate, PPG-1 hydroxyethyl caprylamide, PPG-2 cocamide, a poly(sodium styrene sulfonate), and mixtures thereof;
(f) 0% to about 1.5%, by weight, of a foam stabilizer selected from the group consisting of a $C_{10}$–$C_{22}$ fatty alcohol, a $C_{10}$–$C_{22}$ fatty acid, and mixtures thereof;
(g) 0% to about 5%, by weight, of a humectant; and
(h) water,
wherein the composition contains at least one of (f) and (g),
and wherein the antimicrobial agent is present in an amount of at least 40% of saturation concentration, when measured at room temperature.

2. The composition of claim 1 containing each of (f), and (g).

3. The composition of claim 1 having a log reduction against Gram positive bacteria of at least 2 after 30 seconds of contact, as measured against *S. aureus*.

4. The composition of claim 1 having a log reduction against Gram negative bacteria of at least 2.5 after 30 seconds of contact, as measured against *E. coli*.

5. The composition of claim 1 having a log reduction against Gram positive bacteria of at least 2 after 30 seconds of contact, as measured against *S. aureus*, and a log reduction against Gram negative bacteria of at least 2.5 after 30 seconds of contact, as measured against *E. coli*.

6. The composition of claim 1 wherein the antibacterial agent is present in an amount of at least 50% of saturation concentration.

7. The composition of claim 1 wherein the antibacterial agent is present in an amount of at least 75% of saturation concentration.

8. The composition of claim 1 comprising about 0.05% to about 2% by weight, of the phenolic antibacterial agent.

9. The composition of claim 1 wherein the surfactant is present in an amount of about 0.5% to about 15%, by weight of the composition.

10. The composition of claim 1 wherein the surfactant comprises an anionic surfactant.

11. The composition of claim 1 wherein the surfactant comprises an ampholytic surfactant.

12. The composition of claim 1 wherein the surfactant is selected from the group consisting of a $C_8$–$C_{18}$ alkyl sulfate, an alkamidopropyl betaine, an alkylglucoside, a $C_8$–$C_{18}$ alkamine oxide, and mixtures thereof.

13. The composition of claim 1 wherein the surfactant comprises lauryl sulfate, octyl sulfate, 2-ethylhexyl sulfate, cocamidopropyl betaine, cocoglucoside, lauramine oxide, and mixtures thereof.

14. The composition of claim 1 having a pH of about 5 to about 8.

15. The composition of claim 1 wherein the hydrotrope is present in an amount of about 5% to about 20% by weight.

16. The composition of claim 1 wherein the hydrotrope is selected from the group consisting of sodium cumene sulfonate, ammonium cumene sulfonate, ammonium xylene sulfonate, potassium toluene sulfonate, sodium toluene sulfonate, sodium xylene sulfonate, toluene sulfonic acid, xylene sulfonic acid, sodium polynaphthalene sulfonate, sodium polystyrene sulfonate, sodium methyl naphthalene sulfonate, disodium succinate, and mixtures thereof.

17. The composition of claim 1 wherein the hydric solvent is present in an amount of about 5% to about 15% by weight.

18. The composition of claim 1 wherein the hydric solvent comprises an alcohol, a diol, and mixtures thereof.

19. The composition of claim 18 wherein the hydric solvent comprises methanol, ethanol, isopropyl alcohol, n-butanol, n-propyl alcohol, ethylene glycol, propylene glycol, diethylene glycol, dipropylene glycol, tripropylene glycol, hexylene glycol, butylene glycol, PEG-4, or mixtures thereof.

20. The composition of claim 1 wherein the skin care agent is selected from the group consisting of a derivatized guar gum, hydroxyethylcellulose, hydroxypropylmethylcellulose, a derivatized hydroxyethylcellulose, a polyethylene glycol, a methoxypolyethylene glycol, a hydrolyzed wheat protein, a polyoxyethylene stearyl ether, and an ethoxylated glyceryl $C_8$–$C_{18}$ ester.

21. The composition of claim 1 wherein the foam stabilizer is selected from the group consisting of cetyl alcohol, cetearyl alcohol, stearic acid, and mixtures thereof.

22. The composition of claim 1 wherein the humectant is selected from the group consisting of glycerin, sodium pyrrolidone carboxylate, and mixtures thereof.

* * * * *